US005377006A

United States Patent [19]

Nakata

[11] Patent Number: 5,377,006

[45] Date of Patent: Dec. 27, 1994

[54] METHOD AND APPARATUS FOR DETECTING PHOTOACOUSTIC SIGNAL

[75] Inventor: Toshihiko Nakata, Hiratsuka, Japan

[73] Assignee: Hitachi, Ltd., Tokyo, Japan

[21] Appl. No.: 886,014

[22] Filed: May 20, 1992

[30] Foreign Application Priority Data

May 20, 1991 [JP] Japan .................................. 3-114361
Jun. 25, 1991 [JP] Japan .................................. 3-152955

[51] Int. Cl.$^5$ .......................... G01B 9/02; G01B 11/06

[52] U.S. Cl. .................................... 356/349; 356/351; 356/357; 356/360

[58] Field of Search ............... 356/349, 351, 357, 358, 356/359, 360

[56] References Cited

U.S. PATENT DOCUMENTS

| | | | |
|---|---|---|---|
| 4,457,162 | 7/1984 | Rush et al. | 73/24 |
| 4,854,710 | 8/1989 | Opsal et al. | 356/432 |
| 4,921,346 | 5/1990 | Tokumoto et al. | 356/432 X |
| 4,952,063 | 8/1990 | Opsal et al. | 356/445 X |
| 5,062,715 | 11/1991 | Nakata et al. | 356/432 |
| 5,083,869 | 1/1992 | Nakata et al. | 356/432 |
| 5,085,080 | 2/1992 | Yu | 73/579 |
| 5,136,172 | 8/1992 | Nakata et al. | 250/572 |
| 5,298,970 | 3/1994 | Takamatsu et al. | 356/349 |

OTHER PUBLICATIONS

Chen et al. "New Technique of Photodisplacement Imaging Using One Laser for Both Excitation and Detection", vol. 50, pp. 1349–1351, 1987.

*Primary Examiner*—Robert J. Warden
*Assistant Examiner*—Robert Carpenter
*Attorney, Agent, or Firm*—Antonelli, Terry, Stout & Kraus

[57] ABSTRACT

A photoacoustic signal detection method for detecting information about a surface of a sample and a subsurface of the sample, including the steps of producing an optical frequency difference between an intensity-modulated excitation/probe light beam and a reference light beam, focusing the intensity-modulated excitation/probe light beam on the surface of the sample to generate a photoacoustic effect or a photothermal effect at the surface of the sample, thereby producing thermal distortions in the sample, causing heterodyne interference to occur between a reflected intensity-modulated excitation/probe light beam from the surface of the sample and the reference light beam to produce heterodyne interference light including a frequency component having a frequency equal to twice the intensity modulation frequency, converting the heterodyne interference light to an electric signal including a frequency component having a frequency equal to twice the intensity modulation frequency, extracting from the electric signal at least one of an amplitude and a phase of the frequency component having the frequency equal to twice the intensity modulation frequency, and detecting information about the surface of the sample and the subsurface of the sample based on the extracted at least one of the amplitude and the phase.

32 Claims, 18 Drawing Sheets

F I G. 28
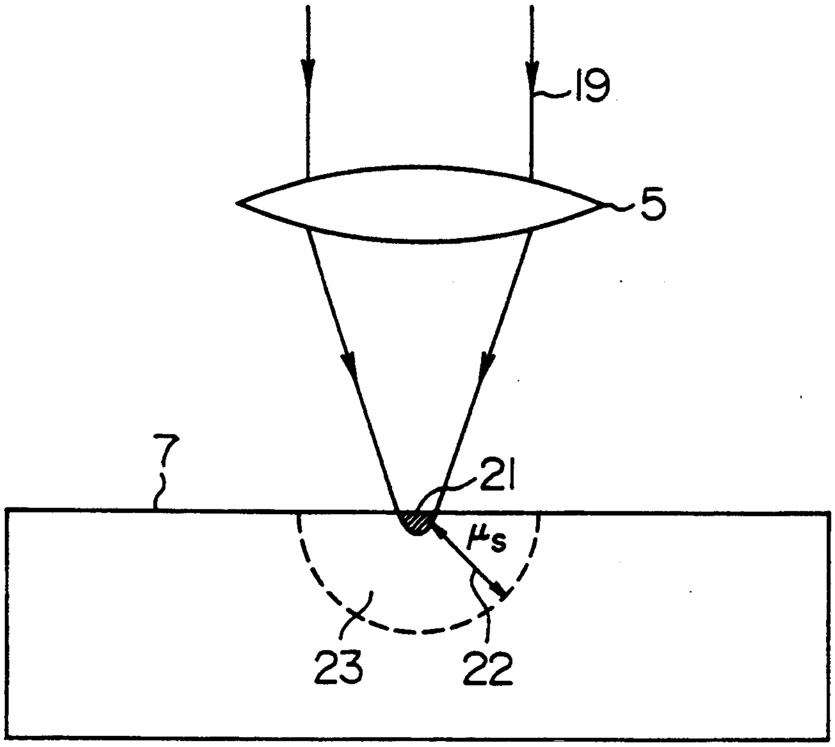

METHOD AND APPARATUS FOR DETECTING PHOTOACOUSTIC SIGNAL

CROSS-REFERENCES TO RELATED APPLICATIONS

U.S. patent applications Ser. No. 479,712 filed on Feb. 14, 1990, now U.S. Pat. No. 5,062,715, and Ser. No. 567,319 filed on Aug. 14, 1990, both relate to detecting a photoacoustic signal as does the present application and are assigned to the assignee of the present application.

BACKGROUND OF THE INVENTION

The present invention relates to a method and a device for detecting a photoacoustic signal for detecting information relative to the surface and subsurface of a sample using the photoacoustic or photothermal effect.

PRIOR ART

The photoacoustic effect was discovered by Tyndall, Bele, Röntgen, et al. in 1881. As shown in FIG. 28, when intensity-modulated light (intermittent light beam) 19 is irradiated to a sample 7 by focusing the light as an excitation light with a lens 5, heat is generated in a light absorption region $V_{op}$ 21 and periodically diffused through a heat diffusion region $V_{th}$ 23 defined by a thermal diffusion length $\mu s$ 22 so that the thermal distortion wave thus generated provides a thermoelastic wave. By detecting this ultrasonic wave i.e. a photoacoustic wave by a microphone (acoustic-electric converter) or a piezo-electric transducer to obtain the component in synchronism with the modulation frequency of the incident light, information relative to the surface and subsurface of the sample can be obtained. A technique for detecting the above photoacoustic signal is disclosed, for example, in "HIHAKAI KENSA", Vol. 36, No. 10 pp. 730–736, October 1987 (Showa 62) or IEEE; 1986 ULTRASONIC SYMPOSIUM—pp. 515–516 (1986).

Now, referring to FIG. 27, one example of such a technique will be explained. A light beam emitted from a laser 1 is intensity-modulated by an acousto-optical modulator (AOM) 2. The thus obtained intermittent light is expanded to a parallel beam 19 of a desired diameter by a beam expander 3, which is reflected by a beam splitter or a half mirror 4 and thereafter focused on the surface of a sample 7 placed on an XY stage 6 by a lens 5. Then, the heat distortion wave created at a focusing position 21 on a sample 7 generates a thermoelastic wave and also provides a minute displacement on the surface of the sample 7. This minute displacement is detected by a Michelson interferometer explained below. Parallel light emitted from a laser 8 is expanded to a beam of a desired diameter by a beam expander 9. This beam is separated into two optical paths by a beam splitter or a half mirror 10. One is focused on the focusing position 21 on the sample 7 by a lens 5 whereas the other is irradiated to a reference mirror 11. Then, the light reflected from the sample 7 and the light reflected from the reference mirror 11 interfere with each other on the beam splitter 10. The interference pattern thus formed is focused on a photoelectric converting element 13 such as a photodiode through a lens 12 to provide a photoelectric-converted interference intensity signal. This interference intensity signal is amplified by a preamplifier 14 and thereafter applied to a lock-in amplifier 16. The lock-in amplifier 16, using as a reference signal a modulation frequency signal from an oscillator 15 used for driving the acousto-optical modulator 2, extracts only the modulated frequency component contained in the interference intensity signal. This frequency component has information relative to the surface or inside of the same according to the frequency. By varying the modulated frequency, the thermal diffusion length $\mu s$ 21 can be changed and the information in a direction of the depth of the sample can be obtained. If there is a defect such as a crack inside a thermal diffusion region $V_{th}$ 23, the modulated frequency component in the interference intensity signal changes to exhibit a signal change so that the presence of the defect can be detected. An XY stage shifting signal and an output signal from the lock-in amplifier 16 are processed by a computer 17. Accordingly, the photoacoustic signals corresponding to the respective positions on the sample can be displayed as two-dimensional image information on a display 18 such as a monitor television.

The above-described prior-art technique is very efficient in that it enables a photoacoustic signal to be detected in a non-contact and non-destruction manner, but also has the following two problems.

A first problem is as follows. According to the conventional optical system as shown in FIG. 27, it is necessary to irradiate the two beams independently on the sample; an excitation light for generating a photoacoustic effect on the surface and inside the sample, and a probe light for detecting minute displacement on the sample surface generated by the photoacoustic effect. Accordingly, in order to detect the photoacoustic effect generated by the excitation light at high resolutions and at high sensitivity, the excitation light and the probe light must be focused on the same point on the sample with a precision of the submicron order. However, it is extremely difficult to adjust the two light beams on the optical axis in this high precision, and, for this purpose, it is necessary to maintain the stability of the optical system at a high level, which results in a very complex optical system and a complex peripheral mechanism.

A second problem is as follows. In general, the signal intensity of a photoacoustic signal is inversely proportional to the intensity modulation frequency of an excitation light. The detection sensitivity of the Michelson interferometer shown in FIG. 27 is inversely proportional to $\sqrt{f}$, where f is a variable frequency of the surface displacement, or the intensity-modulated frequency of the excitation light. When a PZT element is used for detecting a photoacoustic signal, the detection sensitivity changes in accordance with a frequency characteristic of the PZT element. Therefore, according to the conventional photoacoustic signal detector, when defects at different depths within the sample have been detected by changing the intensity modulation frequency of the excited light and when an attempt is made to decide a size of each defect based on the detected photoacoustic signal, it is difficult to quantitatively decide the size of the defect because the signal intensity of the photoacoustic signal changes depending on the modulation frequency as described above.

SUMMARY OF THE INVENTION

In order to solve the above-described first problem, it is a first object of the present invention to provide a method and an apparatus for detecting a photoacoustic signal which enables state detection of information on a surface and inside of a sample with a simple structure without requiring an adjustment of relative optical axes of an excitation light for generating a photoacoustic effect and of a probe light for detecting minute displacement of the sample surface generated by the photoacoustic effect.

In order to achieve the above object, in accordance with one aspect of the present invention, of two beams of mutually different frequencies, one beam is intensity-modulated and focused on a sample to generate a photoacoustic effect, its reflection beam and the other beam are made to interfere with each other to detect therefrom a modulation frequency component which is double that of the other beam so that minute displacements of the sample surface generated by the photoacoustic effect are detected, and information of amplitude and phase corresponding to the intensity-modulated frequency is extracted as a photoacoustic signal from the detected minute displacement signal. With this arrangement, by using one beam, it is possible to generate a photoacoustic effect and to detect minute displacement of the sample surface generated from the photoacoustic effect, and it is not necessary to carry out a relative adjustment of optical axes of the excitation light and the probe light. Further, this simple structure of the optical system enables a stable detection at high sensitivity of the information relative to the surface and the inside of the sample.

Further, according to the present invention, in order to achieve the above object, a difference of frequencies between the two beams is made larger than the above intensity-modulated frequency of the excitation light so as to facilitate the extraction of the amplitude and phase information corresponding to the intensity-modulated frequency from the interference beam detection signal.

Further, in order to achieve the above object, according to the present invention, a frequency shift is generated in only one of the excitation beam and the probe beam to provide a relative optical frequency difference between the two beams, providing a more simple structure of the optical system that enables a stable and high-sensitivity detection of information relative to the surface and inside of the sample.

Further, in order to achieve the above object, according to the present invention, mutually different frequency shifts are generated in both beams to provide a relative difference of optical frequency, enabling an adjustment of an optical frequency difference and a setting of a lower optical frequency difference, thus enabling a stable and high-sensitivity detection of information relative to the surface and inside of the sample.

Further, in order to achieve the above object, according to the present invention, an exciting unit for intensity-modulating one of two beams of which frequencies are mutually different and focusing the intensity-modulated beam on the sample and an optical interference detecting unit for causing an interference between a reflected beam of the focused beam and the other beam to generate minute displacement on the surface of the sample by a photoacoustic effect and detecting this minute displacement, are structured as a confocal optical system, to thereby improve resolution of the photoacoustic signal in the lateral direction, detection sensitivity and a signal SN ratio respectively.

In order to solve the second problem, it is a second object of the present invention to provide a method and an apparatus for detecting a photoacoustic signal which effectively corrects a signal intensity of the photoacoustic signal corresponding to each modulation frequency so that detection sensitivity or signal output intensity is always constant regardless of the intensity-modulated frequency of the excited beam and which enables a stable detection of information relative to the surface and the inside of the sample and a quantitative analysis of the detected information.

In order to achieve the above object, according to another aspect of the present invention, the apparatus for detecting an photoacoustic signal focuses an intensity-modulated beam on a sample, generates a photoacoustic effect or a photothermal effect either on the surface or inside of the sample, detects a thermal distortion on the sample surface generated by the photoacoustic effect or the photothermal effect, detects frequency components of an intensity modulation frequency from the detected signal, and then extracts information relative to the surface or inside of the sample according to the modulation frequency from the frequency components. Further, the apparatus effectively adjusts and compensates the detection sensitivity corresponding to each modulation frequency, to enable a stable detection of information relative to the surface and inside of the sample and a quantitative analysis of the detected information.

Further, in order to achieve the above object, according to the present invention, intensity of the intensity-modulated light is adjusted corresponding to each modulation frequency so that detection sensitivity is constant for each modulation frequency, thus reducing an influence of non-optical noise.

Further, in order to achieve the above object, according to the present invention, intensity of the detected signal is adjusted corresponding to each modulation frequency so that detection sensitivity is constant for each modulation frequency, thus increasing the stability of the optical system.

Further, in order to achieve the above object, according to the present invention, detection sensitivity, including modulation frequency characteristics of a thermal distortion detecting unit for detecting the thermal distortion, is adjusted so that it becomes constant for each modulation frequency, thus improving the quantitativeness of the detected signal.

Further, in order to achieve the above object, according to the present invention, thermal distortion of the surface of the sample is detected by using an optical interference so that a photoacoustic signal can be detected in a non-contact state.

Further, in order to achieve the above object, according to the present invention, thermal distortion of the surface of the sample is detected by using a piezoelectric element, to simplify the structure of the detecting system and improve stability of signal detection.

Further, in order to achieve the above object, according to the present invention, an exciting unit for focusing an intensity-modulated light on a sample and generating a photoacoustic effect or a photothermal effect either on the surface or inside of the sample is structured as a confocal optical system, thus improving the resolution of the photoacoustic signal in the lateral direction, detection sensitivity and a signal SN ratio, respectively.

Further, in order to achieve the above object, according to the present invention, an optical interference detecting unit for detecting thermal distortion on the surface of the sample generated by the photoacoustic effect or the photothermal effect is structured as a confocal optical system, thus improving the resolution of the photoacoustic signal in the lateral direction, detection sensitivity and a signal SN ratio.

BRIEF DESCRIPTION OF THE DRAWINGS

FIG. 28 is a diagram for showing the principle of a photoacoustic effect.

DESCRIPTION OF THE PREFERRED EMBODIMENTS

Embodiments for achieving the first object of the present invention will be explained with reference to FIGS. 1–3, 4(*a*)–4(*b*), 5(*a*)–5(*b*), and 6–14.

Figure 1:
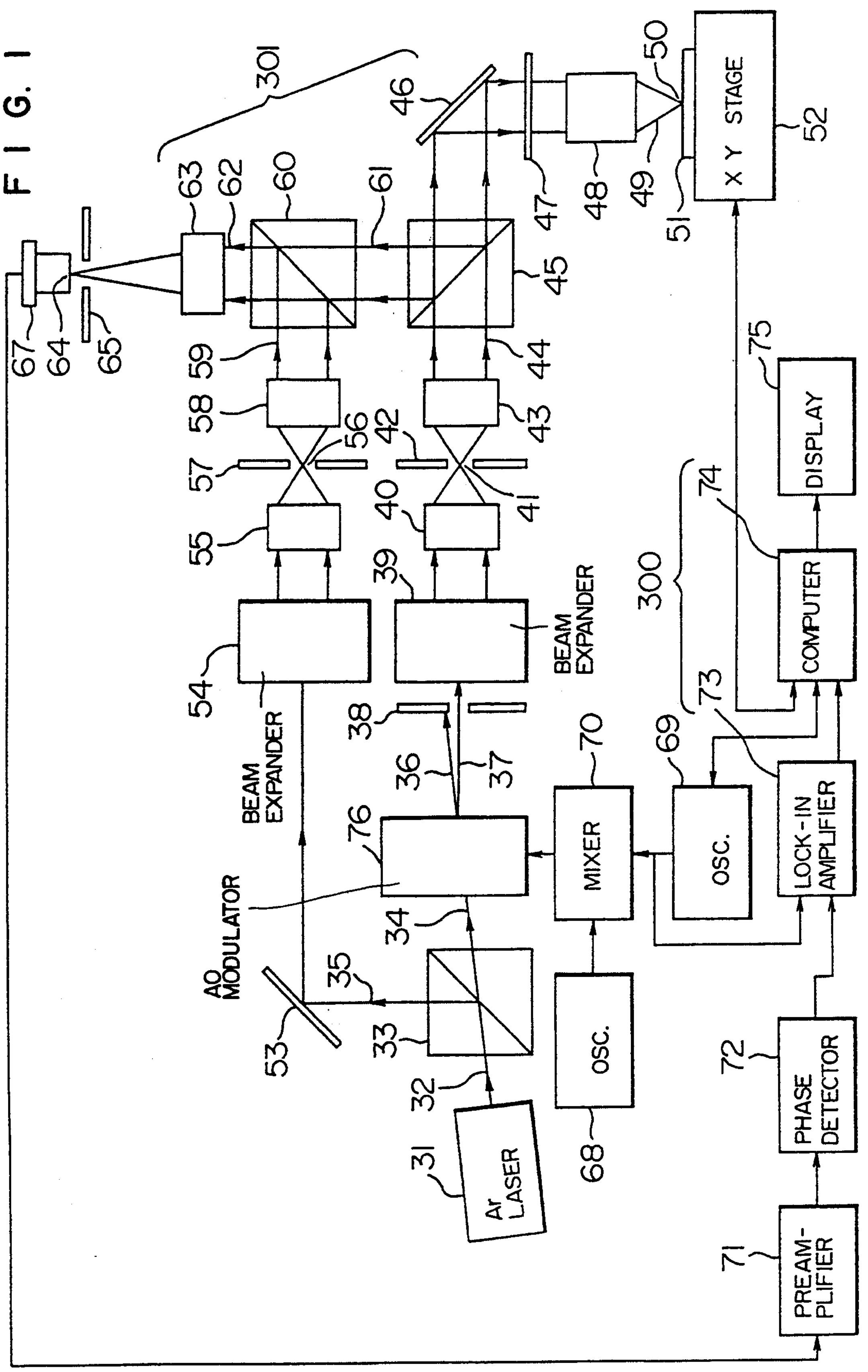
FIG. 1 is a diagram for showing a photoacoustic detecting optical system according to a first embodiment of the present invention.
Figure 2:
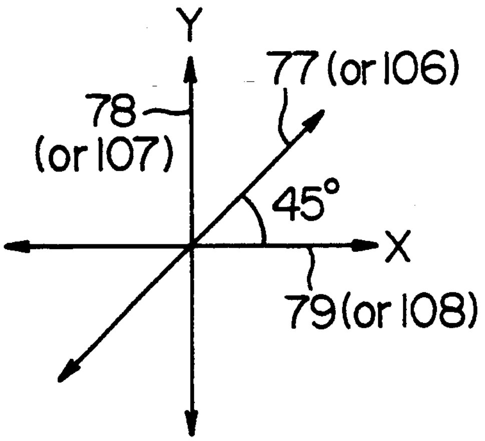
FIG. 2 is a diagram for showing a polarization direction of an incident beam in the first embodiment of the present invention.
Figure 3:
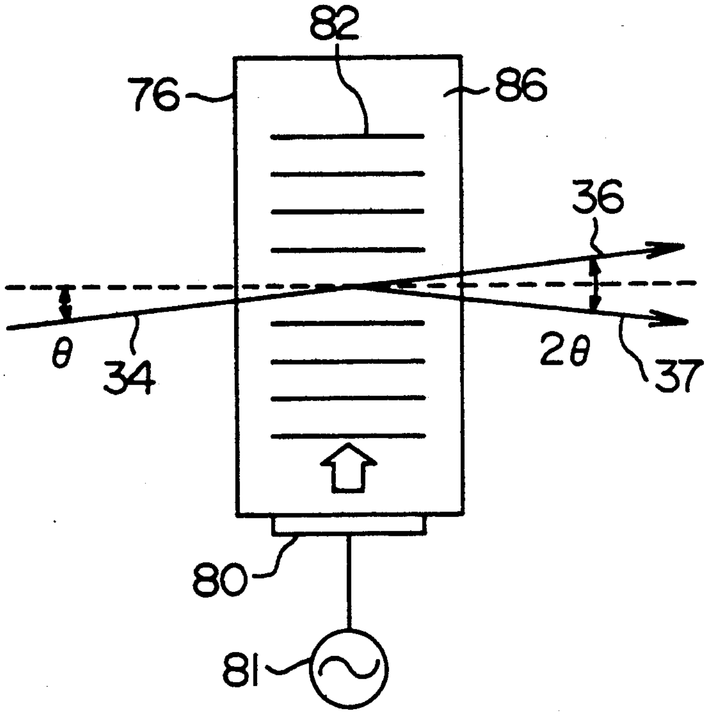
FIG. 3 is a diagram showing the principle of an acousto-optical modulator.
Figure 4A:
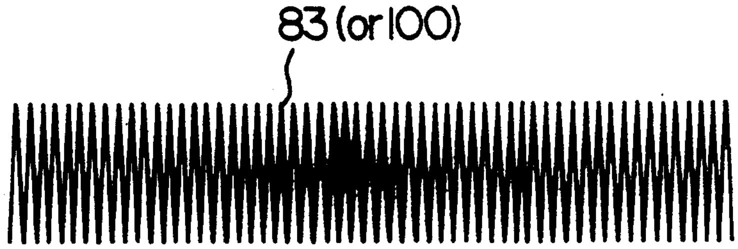
FIGS. 4(*a*)–4(*c*) show waveform diagrams of light signals modulated to be inputted to the acousto-optical modulator.
Figure 4B:
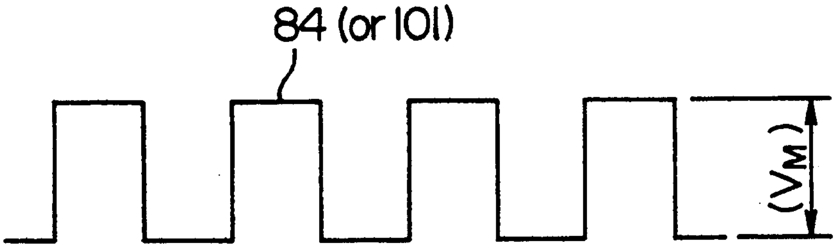
Figure 4C:

At first, the first embodiment of the present invention will be explained with reference to FIGS. 1–3, 4(*a*)–4(*b*), and 5–7. FIG. 1 shows the photoacoustic detecting optical system according to the first embodiment of the present invention. This optical system includes of a heterodyne type Mach-Zehender optical interferometric system 301 working as an excitation optical system and a detecting optical system and a signal processing system 300. In the system 301, a polarization direction of a linear polarization beam 32 emitted from an Ar laser 31 is set to have an angle of 45 degrees with respect to the X axis and Y axis respectively as shown by 77 in FIG. 2. Assume the vertical direction relative to the paper surface of FIG. 1 is expressed by the X axis and the direction orthogonal to the X axis is expressed by the Y axis. Then, by a polarization beam splitter 33, a p-polarization component 34 shown by 78 in FIG. 2 of an incident beam 32 passes through the polarization beam splitter 33 and is applied to an acousto-optical modulator 76. On the other hand, an s-polarization component 35 shown by 79 in FIG. 2 is reflected by the polarization beam splitter 33. The acousto-optical modulator 76 has a structure having a combination of an ultrasonic wave transducer 80 with an optical medium 86 such as glass or tellurium dioxide ($TeO_2$), as shown in FIG. 3. When a sinusoidal wave 83 with a frequency $f_B$ as shown in FIG. 4(*a*) is applied to the ultrasonic wave transducer 80 from an oscillator 81, an ultrasonic wave 82 is propagated through an optical medium 86 to cause a periodical refraction change. This works as a diffraction grating to diffract a beam 34 passing through the optical medium 86. Referring to FIG. 3, a first order diffracted light 37 is emitted in a direction of deflecting the incident light by $2\theta$. Assume the optical frequency of the incident beam is $f_O$, the optical frequency of a zero-order diffracted light 36 remains $f_O$ as it is, but the optical frequency of the first-order diffracted light 37 becomes $f_O+f_B$ which is a result of being shifted by the drive frequency $f_B$ of the ultrasonic wave. A sinusoidal wave 83 of the frequency $f_B$ shown in FIG. 4(*a*) and a square wave 84 of a frequency $f_L(f_L<f_B)$ shown in FIG.

Figure 5A:
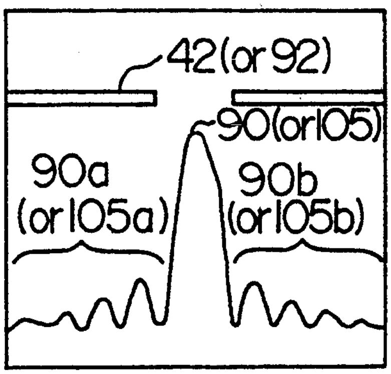
FIGS. 5(*a*)–5(*b*) are views for explaining a manner of shading the high-order diffraction light components of a laser spot.
Figure 5B:
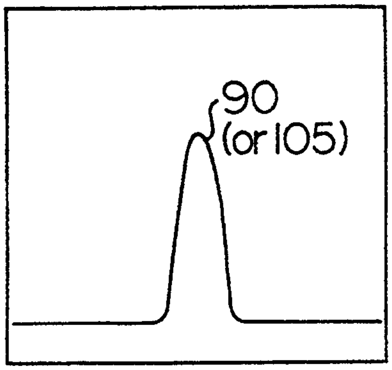

4(*b*) are applied from an oscillator 68 and an oscillator 69 respectively to a mixer 70 in FIG. 1, a product of both waveforms is taken to produce a modulation signal 85 as shown in FIG. 4(*c*), and the modulation signal 85 is applied to the acousto-optical modulator 76. As a result, a first-order diffracted light 37 of p-polarization of which frequency has been shifted by $f_B$ is intermittently outputted at the frequency $f_L$ from the acousto-optical modulator 76. In other words, an intensity-modulated beam having the frequency shift of $f_B$and having the modulation frequency $f_L$ is obtained as an excitation light. The zero-order light 36 is shielded by a diaphragm 38. The intensity-modulated beam 37 is expanded by a beam expander 39 to have a desired beam diameter, and is then focused at a rear focal point 41 by a lens 40. A pin-hole 42 is provided at the rear focal point 41 to shade the high-order diffraction light components 90*a* and 90*b* around a peak part 90 of the focused beam spot as shown in FIG. 5(*a*). As a result, the light intensity distribution immediately after having passed through the pin-hole 42 provides only the peak part 90 as shown in FIG. 5(*b*). Since the focal point 41 is also a front focal point of a lens 43, the light from the pin-hole 42, after having passed through the lens 43, becomes parallel light 44. Being composed of p-polarization components, this parallel light passes through a polarization beam splitter 45 and is reflected from a mirror 46 and then passes through a λ/4 plate 47 where the light is circularly polarized and is focused as a light beam 49 at a front focal point 50, or on a sample 51, through an objective lens 48, to form a light spot having the similar light intensity distribution as shown in FIG. 5(*b*). Namely, the front focal point 41 of the lens 43 and the front focal point 50 of the objective lens 48 are in a conjugate relation and also in a confocal relation. A thermal distortion wave created at the focused spot portion 50 of the sample 51 by the photoacoustic effect generates an ultrasonic wave or a thermoelastic wave and also causes minute displacements on the focused spot portion 50 of the surface of the sample 51. The reflected light from the focused spot portion 50 has phase information representative of the minute displacements of the sample surface and becomes a parallel light after having passed through the objective lens 48, and further becomes an s-polarized beam 61 after passing through the λ/4 plate 47. This s-polarized beam 61 is then reflected by the polarization beam splitter 45 and then passes through a non-polarization beam splitter 60.

Meanwhile, an s-polarized beam 35 reflected from the polarization beam splitter 33, or a reference light, is reflected by a mirror 53, then expanded by a beam expander 54 to have a desired beam diameter, and is then focused at a rear focal point 56 by a lens 55. A pin-hole 57 is provided at the rear focal point 56, to shade the high-order diffraction light components 90*a* and 90*b* around the peak part 90 of the focused beam spot as shown in FIG. 5(*a*). As a result, the light intensity distribution immediately after having passed through the pin-hole 57 provides only the peak part 90 as shown in FIG. 5(*b*). Since the focal point 56 is also a front focal point of a lens 58, the light from the pin-hole 57, after having passed through the lens 58, becomes a parallel reference light 59. The reference light, after having been reflected by a non-diffraction beam splitter 60, mutually interferes with the reflected light 61 from the surface of the sample 51 which has passed through the non-diffraction beam splitter 60. An interference light 62 includes optical phase information representative of minute displacements created on the surface of the sample 51 by the photoacoustic effect. The interference light 62 is focused on a rear focal point 64 by a lens 63 and the focused light is detected by a photoelectric converting element 67 such as a photodiode or the like. In this Mach-Zehender optical interferometric system 301, the front focal point 41 of the lens 43, the front focal point 56 of the lens 58, the front focal point 50 of the objective lens 48 and the rear focal point 64 of the lens 63 are mutually in a conjugate relation and are at the same time in a confocal relation. A pin-hole 65 is provided at the rear focal point 64 of the lens 63 to shade a stray light generated inside the objective lens 48, interference components generated within a transparent thin film on the sample or a high-order diffraction component generated by minute unevenness on the surface of the sample.

It may be noted that such a confocal optical system is specifically described, for example, in U.S. Pat. No. 5,083,869 issued on Jan. 28, 1992.

Assume that the wavelength of the excitation light 32 is expressed as λ, the intensity of the reflected light 61 from the surface of the sample 51 is expressed as Is, the intensity of the reference light 59 is expressed as Ir, the phase difference between two light paths including time variation is expressed as φ(t), the amplitude of minute displacement generated on the surface of the sample 51 is expressed as a, and the phase is expressed as θ, then the intensity I of the interference light detected by the photoelectric converting element 67 is given by the following expression (1).

$$I = \left[ Is + Ir + 2\sqrt{IsIr} \cdot \cos\left\{ 2\pi f_B t - \frac{4\pi}{\lambda} a \cdot \cos(2\pi f_L t + \theta) + \phi(t) \right\} \right] \times \{1 + \cos(2\pi f_L t)\} \tag{1}$$

Since a<λ, the above expression (1) can be further approximated as follows.

$$I \approx \left[ Is + Ir + 2\sqrt{Is \cdot Ir} \cdot \{\cos(2\pi f_B t + \phi(t)) + \sin(2\pi f_B t + \phi(t)) \times \frac{4\pi}{\lambda} a \cdot \cos(2\pi f_L t + \theta\} \right] \times \{1 + \cos(2\pi f_L t)\} \tag{2}$$

In the above expression, a·cos $(2\pi f_L t+\theta)$ is a term for showing minute displacement on the surface of the sample 51 generated based on the photoacoustic effect, and the last term 1+cos $(2\pi f_L t)$ shows a periodical change of intensity of the interference light by the excitation light which has been intensity modulated in the frequency $f_L$. In the present embodiment, the following frequencies have been assumed: $f_B$=40 MHz, $f_L$=100 KHz.

Figure 6:
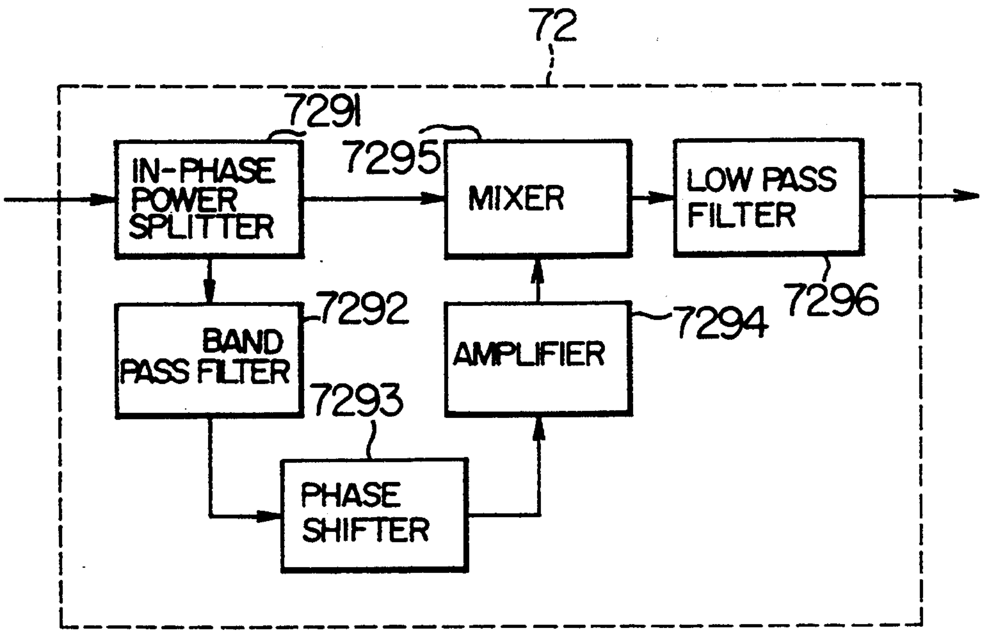
FIG. 6 is a block diagram for showing a phase detecting circuit.

Next a method for detecting the amplitude a and the phase θ of the minute displacement of the surface of the sample 51 generated by the photoacoustic effect from the interference light expressed in the above expression (1) in the signal processing system 300 will be explained. A photoelectrically-converted interference intensity signal is amplified by a preamplifier 71 and is then applied to a phase detecting circuit 72. As shown in FIG. 6, in the phase detecting circuit 72, the detected interference intensity signal is divided into two signals by an in-phase power splitter 7291. One of the divided signals passes through a band pass filter 7292 having a center frequency $f_B$ and is phase-delayed by $\pi/2$ by a phase shifter 7293. An output signal from the phase shifter 7293 is amplified by an amplifier 7294 and is then applied to a mixer 7295. Thus the signal is multiplied with the other interference intensity signal which has been separated by the in-phase power splitter 7291, and then the product signal is produced. The above-described other interference intensity signal $I_{D1}$, the output signal $I_{D2}$ from the amplifier 7294 and the output signal $I_D$ from the mixer 7295 can be expressed by the following expressions (3), (4) and (5), respectively.

$$I_{D1} = \frac{1}{2}\left[Is + Ir + 2\sqrt{IsIr}\cdot\left\{\cos(2\pi f_B t + \theta(t)) + \sin(2\pi f_B t + \phi(t)) \times \frac{4\pi}{\lambda} a\cdot\cos(2\pi f_L t + \theta)\right\}\right] \times \{1 + \cos(2\pi f_L t)\} \quad (3)$$

$$I_{D2} = \sqrt{IsIr}\cdot\{-\sin(2\pi f_B t + \theta(t)) + \cos(2\pi f_B t + \phi(t))\} \quad (4)$$

$$\begin{aligned} I_D &= I_{D1} \times I_{D2} \quad (5)\\ &= \frac{1}{2}(IsIr)\cdot\sqrt{IsIr}\cdot\{-\sin(2\pi f_B t + \phi(t)) + \cos(2\pi f_B t + \phi(t)) - \sin(2\pi f_B t + \phi(t))\cdot\cos(2\pi f_L t) + \cos(2\pi f_B t + \phi(t))\cdot\cos(2\pi f_L t)\} + \\ &\quad IsIr\left[-\frac{4\pi}{\lambda} a\cdot\cos(2\pi f_L t + \theta) + \left\{1 + \frac{4\pi}{\lambda} a\cdot\cos(2\pi f_L t + \theta\right\}\cdot\cos^2(2\pi f_B t + \phi(t)) + \left\{\frac{4\pi}{\lambda} a\cdot\cos(2\pi f_L t + \theta) - 1\right\}\times \cos(2\pi f_B t + \phi(t))\cdot\sin(2\pi f_B t + \phi(t))\right] \times \\ &\quad \{1 + \cos(2\pi f_L t)\} \end{aligned}$$

Since $a < \lambda$, the above expression (5) can be approximated as follows.

$$\begin{aligned} I_D \approx\; & \frac{1}{2}(Is + Ir)\cdot\sqrt{IsIr}\;\{-\sin(2\pi f_B t + \phi(t)) + \cos(2\pi f_B t + \phi(t)) - \sin(2\pi f_B t + \phi(t))\cdot(2\pi f_L t) + \cos(2\pi f_B t + \phi(t))\cdot\cos(2\pi f_L t)\} + \\ & IsIr\left\{\frac{1}{2} - \frac{4\pi}{\lambda} a\cdot\cos(2\pi f_L t + \theta) + \frac{1}{2}\cos(2\pi f_L t) - \frac{4\pi}{\lambda} a\cdot\sin(2\pi f_L t)\cdot\sin(2\pi f_L t + \theta) - \right. \quad (6) \end{aligned}$$

-continued $$\begin{aligned} & \frac{4\pi}{\lambda} a\cdot\cos(4\pi f_L t + \theta) + \frac{1}{2}\cos(4\pi f_B t + 2\phi(t)) - \frac{1}{2}\sin(4\pi f_B t + 2\phi(t)) + \\ & \frac{1}{2}\cos(4\pi f_B t + 2\phi(t))\cdot\cos(2\pi f_L t) - \frac{1}{2}\sin(4\pi f_B t + 2\phi(t))\cdot\cos(2\pi f_L t) \end{aligned}$$

Figure 7:
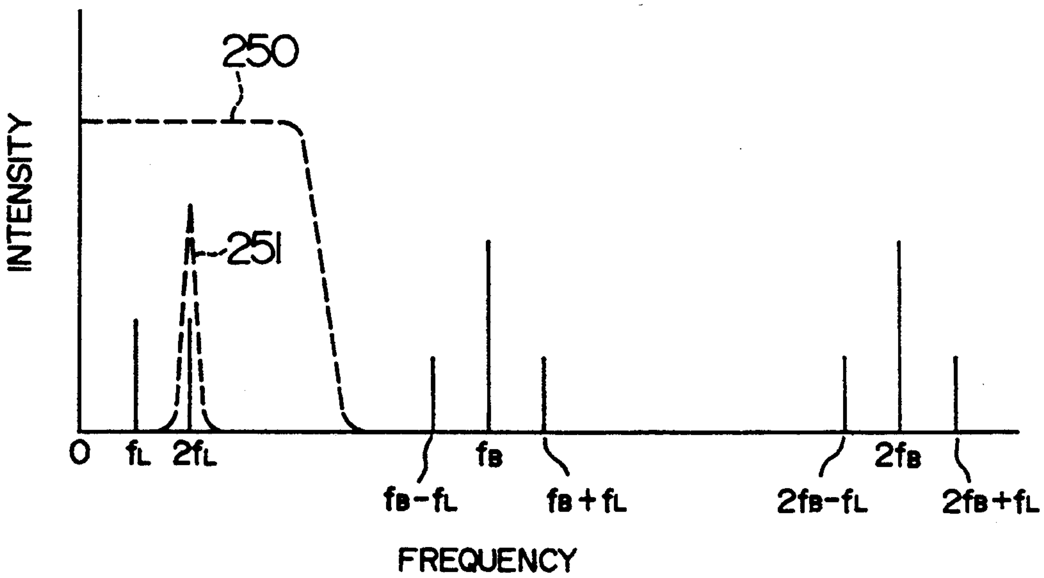
FIG. 7 is a diagram for showing a frequency spectrum of an interference intensity signal.

In the expression (6), it is clear that the first and second terms show the frequency component of $f_B$, the third and fourth terms show the frequency component of $f_B \pm f_L$, the fifth term shows the DC component, the sixth, seventh and eighth terms show the frequency component of $f_L$, the ninth term shows the frequency component of $2f_L$, tenth and eleventh terms show the frequency component of $2f_B$ and the twelfth and thirteenth terms show the frequency component of $2f_B \pm f_L$, respectively. Frequency spectrums of these terms are shown in FIG. 7. The sixth, seventh and eighth terms show the frequency component of $f_L$ which is the same as the modulation frequency of the excitation light. However, it is extremely difficult to obtain from these terms only the amplitude a and the phase $\theta$ of the minute displacement on the surface of the sample 51 which occurred based on the photoacoustic effect. On the other hand, it is easy to obtain only the amplitude a and the phase $\theta$ of the minute displacement from the ninth term which shows the frequency component of $2f_L$, in the following manner. Under the condition of $f_L < f_B - f_L$, an output signal from the mixer 7295 is passed through a low pass filter 7296 having the frequency characteristics shown by a broken line 250 in FIG. 7, and then this output signal is applied to a lock-in amplifier 73 in FIG. 1. In this case, a modulation frequency (frequency $f_L$) from the oscillator 69 is applied to an input terminal of a double frequency reference signal of the lock-in amplifier 73. This modulation signal is converted into a signal of the frequency $2f_L$ inside the lock-in amplifier 73. The DC component and the frequency component of each of $f_L$ and $2f_L$ are outputted from the low pass filter 7296, and the amplitude and the phase of the frequency component of $2f_L$ in the ninth term of the expression (6) are finally extracted from the lock-in amplifier 73. The amplitude a and the phase $\theta$ of the minute displacement on the surface of the sample 51 can be obtained from the outputted amplitude and phase. The amplitude a and the phase $\theta$ have thermal and elastic information within the thermal diffusion region $V_{th}$ defined by the modulation frequency. Accordingly, if there is an internal defect such as a crack within this thermal diffusion region $V_{th}$, the amplitude a and the phase $\theta$ change so that the existence of the internal defect is known. A move control signal of the XY stage 52 and an output signal from the lock-in amplifier 73 are processed by a computer 74, and a photoacoustic signal at each point on the sample 51 is outputted as a two-dimensional photoacoustic image on a monitor television set 75. By controlling the frequency $f_L$ of the modulation signal outputted from the oscillator 69 by the computer 74, the modulation frequency can be set at various values so that internal information of the sample 51 at any depth position can be detected.

For example, thermal diffusion lengths have been detected with various materials as shown by the following table.

TABLE

| μm | Thermal diffusion length $f_L$[Hz] 1k | 5k | 10k | 50k | 100k | 200k |
|---|---|---|---|---|---|---|
| Si | 174 | 78 | 55 | 25 | 17 | 12 |
| Al | 177 | 79 | 56 | 25 | 18 | 13 |
| $SiO_2$ | 15 | 6.9 | 4.9 | 2.2 | 1.5 | 1.1 |
| $Al_2O_3$ | 16~66 | 7~30 | 5~21 | 2~9 | 1.6~6.6 | 1.1~4.7 |
| Au | 202 | 91 | 64 | 29 | 20 | 14 |
| Cu | 193 | 86 | 61 | 27 | 19 | 14 |
| W | 145 | 65 | 46 | 21 | 15 | 10 |
| Air | 76 | 34 | 24 | 11 | 8 | 5 |

Figure 9:
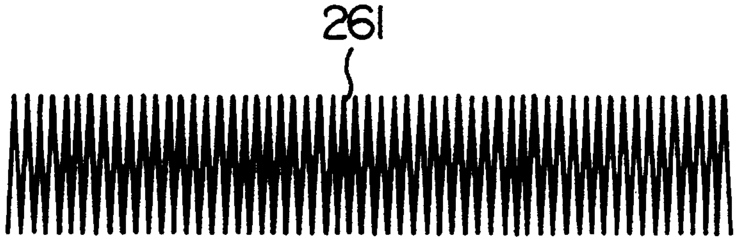
FIG. 9 is a diagram for showing a modulation signal to be inputted to the acousto-optical modulator.
Figure 8:
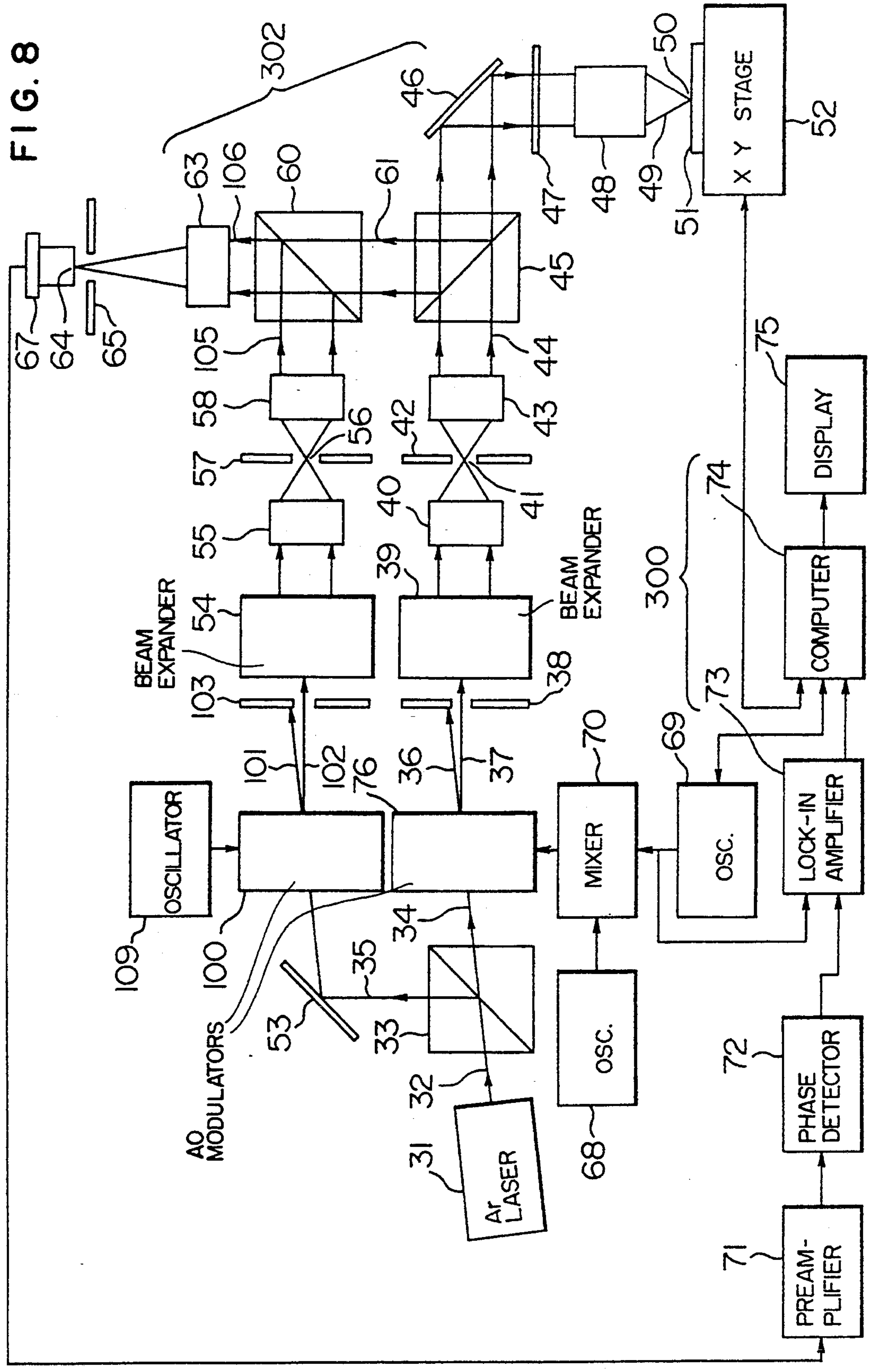
FIG. 8 is a diagram for showing a photoacoustic detecting optical system according to a second embodiment of the present invention.

A second embodiment of the present invention will be explained with reference to FIGS. 8 and 9, showing a photoacoustic detecting optical system. This optical system comprises a heterodyne type Mach-Zehender optical interferometric system 302 working as an excitation optical system and a detecting optical system and a signal processing system 300. The basic structure and the function of this optical system are the same as those of the first embodiment of the present invention shown in FIG. 1, and therefore their detailed explanation will be omitted. The second embodiment is different from the first embodiment in that in the second embodiment, an optical frequency shift of the reference light 35 reflected by the polarization beam splitter 33 is also caused. The frequency shift is caused in the same manner as that of the excitation light in the first embodiment. To be more specific, a sinusoidal wave 261 of a frequency $f_{C2}$ shown in FIG. 9 is outputted from an oscillator 109 and applied to an acousto-optical modulator 100 to obtain a first-order diffraction light 102 having a frequency shifted by $f_{C2}$. A zero-order light 101 is shaded by a diaphragm 103. Regarding the p-polarized component 34 which has passed through the polarization beam splitter 33, the sinusoidal wave 83 of the frequency $f_{C1}$ ($f_{C1} \neq f_{C2}$) shown in FIG. 4(*a*) and the rectangular wave 84 of the frequency $f_L$ ($f_L < f_{C1}$, $f_{C2}$) shown in FIG. 4(*b*) are applied to the mixer 70 from the oscillator 68 and the oscillator 69, respectively, in the same manner as that of the first embodiment, and the product of these waveforms is taken to produce the modulated signal 85 as shown in FIG. 4(*c*). The modulated signal 85 is then applied to the acousto-optical modulator 76. As a result, the p-polarized first-order diffraction light 37 having a frequency shifted by $f_{C1}$ is intermittently outputted from the acousto-optical modulator 76 at the frequency $f_L$. In other words, as the excitation light, an intensity-modulated beam is produced with a frequency shift of $f_{c1}$ and a modulation frequency $f_L$. This excitation light is focused on the sample 51 to generate a photoacoustic effect, and at the same time, the reflected light 61 passes through the non-polarization beam splitter 60 and then mutually interferes with a reference light 105 reflected by the non-polarization beam splitter 60, in the same manner as the first embodiment. An interference light 106 includes optical phase information representative of minute displacements of the surface of the sample 51 generated by the photoacoustic effect. The interference light 106 is focused at the rear focal point 64 by the lens 63 and is then detected by the photoelectric converting element 67 such as a photodiode or the like. In this Mach-Zehender optical interferometric system 302, the front focal point 41 of the lens 43, the front focal point 56 of the lens 58, the front focal point 50 of the objective lens 48 and the rear focal point 64 of the lens 63 are mutually in a conjugate relation and are at the same time in a confocal relation. A pin-hole 65 is provided at the rear focal point 64 of the lens 63 to shade stray light generated inside the objective lens 48, interference components generated within a transparent thin film on the sample or a high-order diffraction component generated by minute unevenness on the surface of the sample.

Assume that the difference of frequencies between the reflected light and the reference light is given as $f_B$. Then, $f_B$ is $f_B = f_{C1} - f_{C2}$, and the intensity of the interference light detected by the photoelectric converting element 67 can be expressed by the expression (1) of the first embodiment in the same manner as is the first embodiment. Accordingly, in the same manner as is the first embodiment, by detecting the frequency component which is two times the modulation frequency $f_L$ from the interference light given by the expression (1), the amplitude a and the phase $\theta$ of the minute displacement on the surface of the sample 51 generated based on the photoacoustic effect can be obtained by the signal processing system 300. In the present embodiment, the following frequencies have been assumed: $f_{C1}=79$ MHz, $f_{C2}=80$ MHz, $f_L=100$ kHz. In other words, $f_B=1$ MHz. As explained above, it is a main feature of the present embodiment that a lower difference of frequencies than that of the first embodiment can be provided between the reflected light from the sample and the reference light by applying mutually different frequency shifts to these two light beams.

Figure 10:
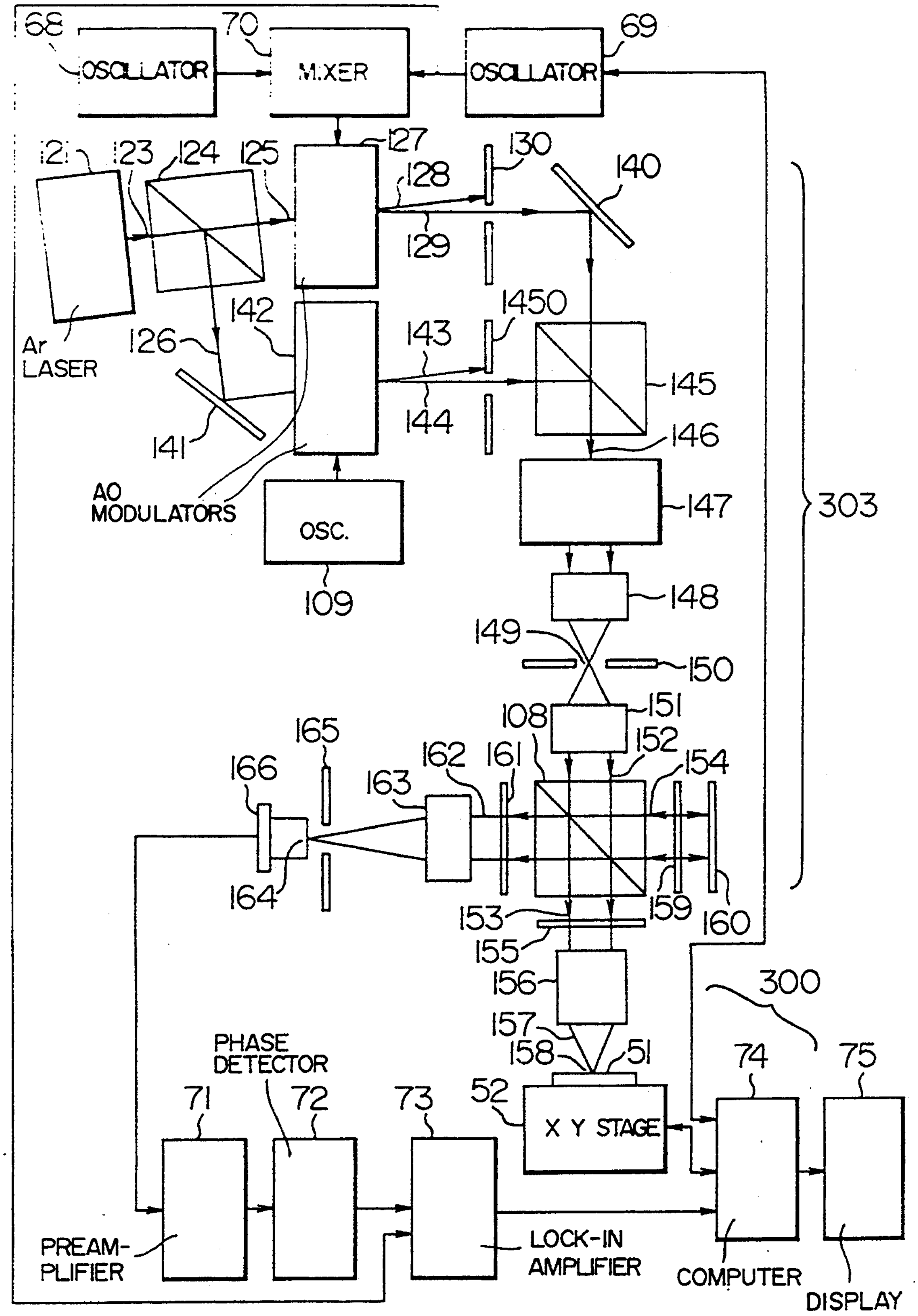
FIG. 10 is a diagram for showing a photoacoustic detecting optical system according to a third embodiment of the present invention.
Figure 11:
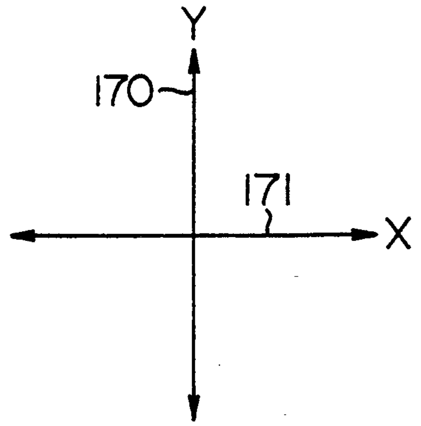
FIG. 11 is a diagram for showing a state of a two-frequency orthogonal polarization in the third embodiment of the present invention.
Figure 12:
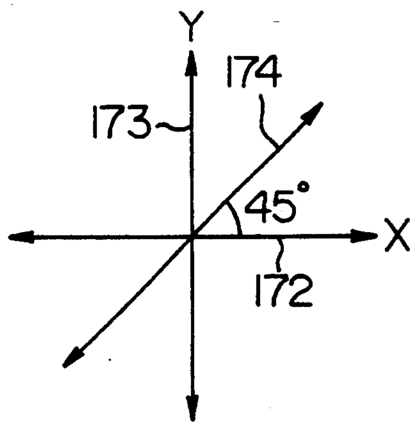
FIG. 12 is a diagram for showing polarization directions of a reflected beam from a sample, a reference beam and a beam from a polarization plate in the third embodiment of the present invention.

A third embodiment of the present invention will be explained with reference to FIGS. 10 to 12. FIG. 10 shows a photoacoustic detecting optical system according to the third embodiment of the present invention. The present optical system comprises a heterodyne type Michelson optical interferometric system 303 which works as an excitation optical system and a detecting optical system and a signal processing system 300. In the Michelson optical interferometric system 303, the polarization direction of a linear polarized beam 123 emitted from an Ar laser 121 is set to have an angle of 45 degrees with respect to the x axis and the y axis respectively as shown by 77 in FIG. 2, in the same manner as that in the first embodiment. Assume the x axis is in the vertical direction relative to the paper surface of FIG. 10 and the y axis is the direction orthogonal thereto Then, a p-polarized component 125 shown by 78 in FIG. 2 passes through a polarization beam splitter 124 and then this is incident to an acousto-optical modulator 127. An s-polarized component 126 shown by 79 in FIG. 2 is reflected by the polarization beam splitter 124. In the same manner as in the first embodiment, the sinusoidal wave 83 of the frequency $f_C1$ shown in FIG. 4(*a*) and the rectangular wave 84 of the frequency $f_L$ ($f_L < f_{C1}$) shown in FIG. 4(*b*) are applied to the mixer 70 from the oscillator 68 and the oscillator 69 respectively. A signal of product of these waveforms is taken to produce the modulation signal 85 as shown in FIG. 4(*c*), and this is applied to the acousto-optical modulator 127. As a result, a p-polarized first-order diffraction light 129 which is a result of the frequency having been shifted by $f_{C1}$ is intermittently outputted at the frequency $f_L$ from the acousto-optical modulator 127. A zero-order light 128 is shaded by a diaphragm 130. The p-polarized first-order diffraction light 129 is reflected by a mirror 140 and then passes through a polarization beam splitter 145. On the other hand, an s-polarized component 126 which has been reflected by the polarization beam splitter 124 is reflected by a mirror 141 and is then incident to the acousto-optical modulator 142. The sinusoidal wave 261 of the frequency $f_{C2}$ ($f_{C1} \neq f_{C2}$) shown in FIG. 9 outputted from the oscillator 109 is inputted to an acousto-optical modulator 142, to obtain a first-order diffraction light 144 which is a result of the frequency having been shifted by $f_{C2}$. A zero-order light 143 is shaded by the diaphragm 1450. The s-polarized first-order diffraction light 144 is reflected by the polarization beam splitter 145, and is combined with the p-polarized diffraction light 129 which has passed through the polarization beam splitter 145. A combined light 146 has orthogonal polarized components having two different frequencies. In other words, the combined light 146 is formed by light of beams having mutually orthogonal polarization directions 170 and 171 as shown in FIG. 11, and having a frequency difference of $f_{C1}$-$f_{C2}$ therebetween. The combined light beam 146 is expanded by a beam expander 147 to have a desired beam diameter, and is then focused at a rear focal point 149 of a lens 148. A pin-hole 150 is provided at the rear focal point 149 to shade the high-order diffraction light components 90*a* and 90*b* around the peak portion 90 of the focal spot as shown in FIG. 5(*a*). As a result, the light intensity distribution passing through the pin-hole 150 provides only the peak portion 90 as shown in FIG. 5(*b*). Since the focal point 149 is positioned as the front focal point of the lens 151, the light passing through the pin-hole 150 becomes a parallel light. The parallel light is divided into a p-polarized beam 153 and an s-polarized beam 154 by a polarization beam splitter 108. The p-polarized beam 153 has the optical frequency shift of $f_{C1}$ and intensity modulated at the modulation frequency $f_L$. The p-polarized beam 153, after having passed through a λ/4 plate 155, is circularly polarized and is focused, as an excitation light, at a front focal point 158 that is the surface of the sample 51 by an objective lens 156 to become a light spot having the light intensity distribution similar to the one as shown in FIG. 5(*b*). In other words, the front focal point 149 of the lens 151 and the front focal point 158 of the objective lens 156 are mutually in a conjugate relation and at the same time are in a confocal relation. A thermoelastic wave is generated at the focal point 158 on the sample 51 based on the photoacoustic effect, and at the same time, minute displacement of the sample surface occurs at the focal position 158 on the sample 51. A reflected light from the focal point 158 has phase information representative of the minute displacement of the sample surface, and becomes a parallel light after having passed through the objective lens 156. The parallel light, after having passed through the λ/4 plate 155, becomes an s-polarized beam, which is then reflected by the beam polarization splitter 108.

In the mean time, the s-polarized beam 154 separated by the polarization beam splitter 108 has the optical frequency shift of $f_{C2}$ and is circularly polarized after passing through the λ/4 plate 159. The beam is then incident to a reference mirror 160. The circularly polarized beam after having been reflected by the reference mirror 160 passes through the λ/4 plate 159 again and is then p-polarized, and passes through the polarization beam splitter 108 as a reference light. 172 in FIG. 12 shows a polarization direction of the reflected light from the sample 51 reflected by the polarization beam splitter 108, and 173 in FIG. 12 shows a polarization direction of the reflected beam from the reference mirror 160. Since the polarization directions of both lights are mutually orthogonal with each other, they do not interfere with each other in this state. When a polarization plate 161 is inserted in their light path with a polarization direction set to have an angle of 45 degrees as shown by 174 in FIG. 12, both reflected lights interfere with each other. This interference light 162 includes optical phase information representative of the minute displacement of the surface of the sample 51 generated by the photoacoustic effect. The interference light 162 is focused on a rear focal point 164 by the lens 163 and the focused light is detected by a photoelectric converting element 166 such as a diode or the like. In this Michelson optical interferometric system 300, the front focal point 149 of the lens 151, the front focal point 158 of the objective lens 156 and the rear focal point 164 of the lens 163 are mutually in a conjugate relation and are at the same time in a confocal relation. Further, a pinhole 165 is provided at the rear focal point 164 of the lens 163. As a result, a stray light generated within the objective lens 156, an interference component generated within a transparent thin film on the sample and a high-order diffraction component generated by a fine unevenness on the sample surface can be shaded.

Assume the difference of frequency between the reflected light from the sample and the reference light from the reference mirror to be $f_B$. Then, $f_B$ has the relation of $f_B = f_{C1} - f_{C2}$, and the intensity I of the interference light detected by the photoelectric converting element 166 is expressed by the expression (1) in the same manner as in the first embodiment. Accordingly, in the same manner as in the first embodiment, by using the signal processing system 300 and detecting the frequency component which is double the modulation frequency $f_L$ from the interference light given by the expression (1), it is possible to obtain the amplitude a and the phase θ of the minute displacement of the surface of the sample 51 generated by the photoacoustic effect. In the present embodiment, the following frequencies have been assumed: $f_{C1} = 79$ MHz, $f_{C2} = 80$ MHz, $f_L = 100$ kHz. In other words, $f_B = 1$ MHz. As explained above, it is a main feature of the present embodiment that by causing mutually different frequency shifts of the reflected light from the sample and the reference light, a smaller frequency difference can be provided between the two lights than that in the first embodiment.

Figure 14:
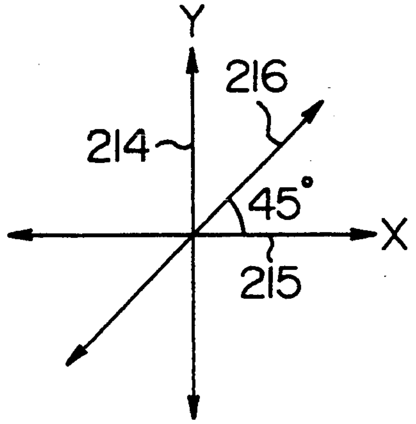
FIG. 14 is a diagram for showing polarization directions of a reflected beam from a sample, a reference beam and a beam from a polarization plate in the fourth embodiment of the present invention.
Figure 13:
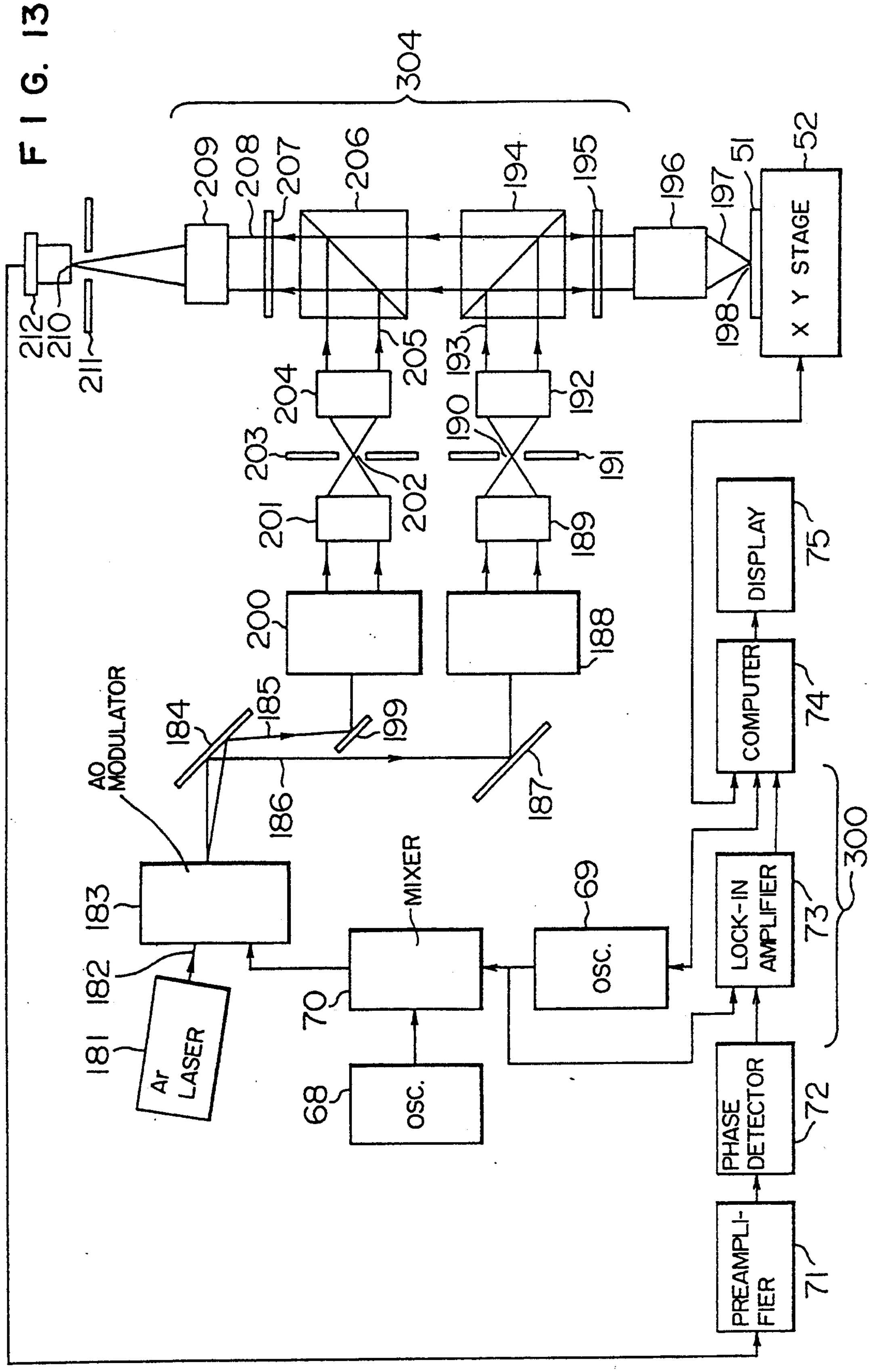
FIG. 13 is a diagram for showing a photoacoustic detecting optical system in the fourth embodiment of the present invention.

A fourth embodiment of the present invention will be explained with reference to FIGS. 13 and 14. FIG. 13 shows an photoacoustic detecting optical system according to the fourth embodiment of the present invention. The present optical system comprises a heterodyne type Mach-Zehender optical interferometric system 304 which works as an excitation optical system and a detecting optical system and a signal processing system 300. In the Mach-Zehender optical interferometric system 304, an s-polarized beam 182 emitted from an Ar laser 181 is incident to an acousto-optical modulator 183. In the same manner as in the first embodiment, the sinusoidal wave 83 of the frequency $f_B$ shown in FIG. 4(*a*) and the rectangular wave 84 of the frequency $f_L$ ($f_L < f_B$) shown in FIG. 4(*b*) are inputted to the mixer 70, from the oscillator 68 and the oscillator 69, respectively and a product of these waveforms is taken, to produce the modulation signal 85 as shown in FIG. 4(*c*). The modulation signal 85 is then inputted to the acousto-optical modulator 183. As a result, the acousto-optical modulator 183 outputs only a zero-order light 185 and a first-order diffraction light 186 having its frequency shifted by $f_B$ and being intensity-modulated by the modulation frequency $f_L$. The first-order diffraction light 186, after having been reflected by a mirror 184 and a mirror 187, is expanded by a beam expander 188 to have a desired beam diameter, and is then focused at a rear focal point 190 by a lens 189. At the rear focal point 190 a pin-hole 191 is provided, to shade the high-order diffraction optical components 90*a* and 90*b* around the peak portion 90 of the light focusing spot as shown in FIG. 5(*a*). As a result, the light intensity distribution of the light after having passed through the pin-hole 191 provides essentially the peak portion 90 as shown in FIG. 5(*b*). Since the focal point 190 is at a front focal point of the lens 192, the light from the pin-hole 191 after having passed through the lens 192 becomes a parallel light 193. The parallel light, consisting of an s-polarization component, is reflected by a polarization beam splitter 194, and is circularly polarized after passing through a λ/4 plate 195. The circularly polarized light is then focused at a front focal point 198 that is on the surface of the sample 51 by an objective lens 196 to form an optical spot having the light intensity distribution similar to the one as shown in FIG. 5(*b*). In other words, the front focal point 190 of the lens 192 and the front focal point 198 of the objective lens 196 are mutually in a conjugate relation and are also in a confocal relation. A thermal distortion wave generated by the photoacoustic effect creates a thermoelastic wave on the focal point 198 on the sample 51, and at the same generates minute displacement at the sample surface at the focal point 198 on the surface of the sample 51. The reflected light from the light focal point 198 has phase information representative of the minute displacement generated on the surface of the sample 51, and becomes a parallel light after passing through the objective lens 196. The parallel light, after passing through the λ/4 plate 195, becomes a p-polarized beam. The p-polarized beam passes through the polarization beam splitter 194 and then passes through a polarization beam splitter 206.

On the other hand, the zero-order light 185 which is a reference light is reflected by the mirror 184 and a mirror 199, then expanded by a beam expander 200, and is focused at a rear focal point 202 by a lens 201 in a manner similar to the one applied to the first-order diffraction light 186. A pin-hole 203 is provided at the rear focal point 202 to shade the high-order diffraction light components 90*a* and 90*b* around the peak portion 90 of the focal spot. As a result, the light intensity distribution of the light after having passed through the pin-hole 203 provides only the peak portion 90 as shown in FIG. 5(*b*). Since the focal point 202 is a front focal point of the lens 204, the light after having passed through the pin-hole 203 becomes a parallel light after passing through the lens 204. The reference light, consisting of an s-polarization component, is reflected by the polarization beam splitter 206 and is then combined with the reflected light from the surface of the sample 51 which has passed through the polarization beam splitter 206. 214 in FIG. 4 shows a polarization direction of the reflected light from the sample 51 after having passed through the polarization beam splitter 206, and 215 in FIG. 14 shows a polarization direction of the reference light reflected by the polarization beam splitter 206. Since the polarization directions of both lights are mutually orthogonal with each other, they do not interfere with each other in this state. Then, a polarization plate 207 is inserted into the light path and its polarization direction is set to have an angle of 45 degrees as shown by 216 in FIG. 14, so that both reflected lights interfere with each other. An interference light 208 includes optical phase information representative of the minute displacement of the surface of the sample 51 generated by the photoacoustic effect. The interference light 208 is focused at a rear focal point 210 by a lens 209, and the focused light is detected by a photoelectric converting element 212 such as a photodiode or the like. In this Mach-Zehender optical interferometric system 304, the front focal point 190 of the lens 192, the front focal point 202 of the lens 204, the front focal point 198 of the objective lens 196 and the rear focal point 210 of the lens 209 are mutually in a conjugate relation and are at the same time in a confocal relation. Further, a pin-hole 211 is provided at the rear focal point 210 of the lens 209. As a result, a stray light generated within the objective lens 196, an interference component generated within a transparent thin film on the sample and a high-order diffraction light component generated by an uneven surface of the sample can be shaded.

Assume that the wavelength of the excitation light is expressed as λ, the intensity of the reflected light from the surface of the sample 51 is expressed as Is, the intensity of the reference light is expressed as Ir, the phase difference between two light paths including time variation is expressed as $\phi(t)$, the amplitude of the minute displacement of the surface of the sample 51 is expressed as a, and the phase is expressed as $\theta$, then the intensity I of the interference light detected by the photoelectric converting element 212 is expressed by the expression (1) of the embodiment 1 in the same manner as in the first embodiment. Accordingly, by detecting the frequency component which is two times the modulation frequency $f_L$ from the interference light expressed by the expression (1), the amplitude a and the phase $\theta$ of the minute displacement of the surface of the sample 51 generated by the photoacoustic effect can be obtained by the signal processing system 300 in the same manner as the one applied in the first embodiment. In the present embodiment, the following frequencies have been assumed: $f_B=40$ kHz, $f_L=100$ kHz.

As described above, according to the first to the fourth embodiments of the present invention, the Mach-Zehender optical interferometric system or the Michelson optical interferometric system based on heterodyne interometry is employed and a frequency component which is two times the modulation frequency of the intensity modulated beam which is an excitation light is detected, so that a reflected light from the sample can be used as a probe light for a photoacoustic detection. As a result, by using one light beam, a photoacoustic effect can be generated and minute displacement which occurred on the sample surface due to this photoacoustic effect can be detected, thus enabling an accurate detection of a photoacoustic signal at the excited part of the sample. Further, a relative adjustment of an optical axis between the excitation light and the probe light becomes unnecessary. Further, with a simple structure of the optical system, a stable and highly sensitive detection of information relative to the surface and the subsurface of the sample is made possible.

Further, according to the fourth embodiment, a zero-order light and the first-order diffracted light outputted from the acousto-optical modulator are used as the reference light and the excitation light respectively, so that loss of light quantity can be minimized.

Further, according to the first to the fourth embodiments of the present invention, the interferometric optical system is structured as a confocal optical system, so that a spot light having an ideal peak portion without an unnecessary high-order diffraction light component can be formed on the sample and on the interference light detecting unit. Further, it is possible to shade any one of a stray light which occurred within the objective lens, an interference component which occurred within a transparent thin film on the sample, such as, for example, a transparent protection film of the semiconductor wafer sample, and a high-order diffraction light component which occurred due to minute unevenness of the surface of the sample. As a result, resolution of the photoacoustic signal in the lateral direction, detection sensitivity and the signal to noise ratio can be improved.

Further, according to the second and the third embodiments of the present invention, mutually different optical frequency shifts are applied to the excitation light or the reflected light from the sample and the reference light to provide a relative optical frequency difference. Therefore, as compared with the first embodiment, a lower optical frequency shift can be set. This also facilitates the extraction of information of an amplitude and phase corresponding to the intensity modulation frequency from the interference light detecting signal in the signal processing system. At the same time, it enables a stable and high-density detection of information relative to the surface and the subsurface or inside of the sample.

Embodiments for achieving the second object of the present invention will now be explained with reference to FIGS. 15 to 26.

Figure 15:
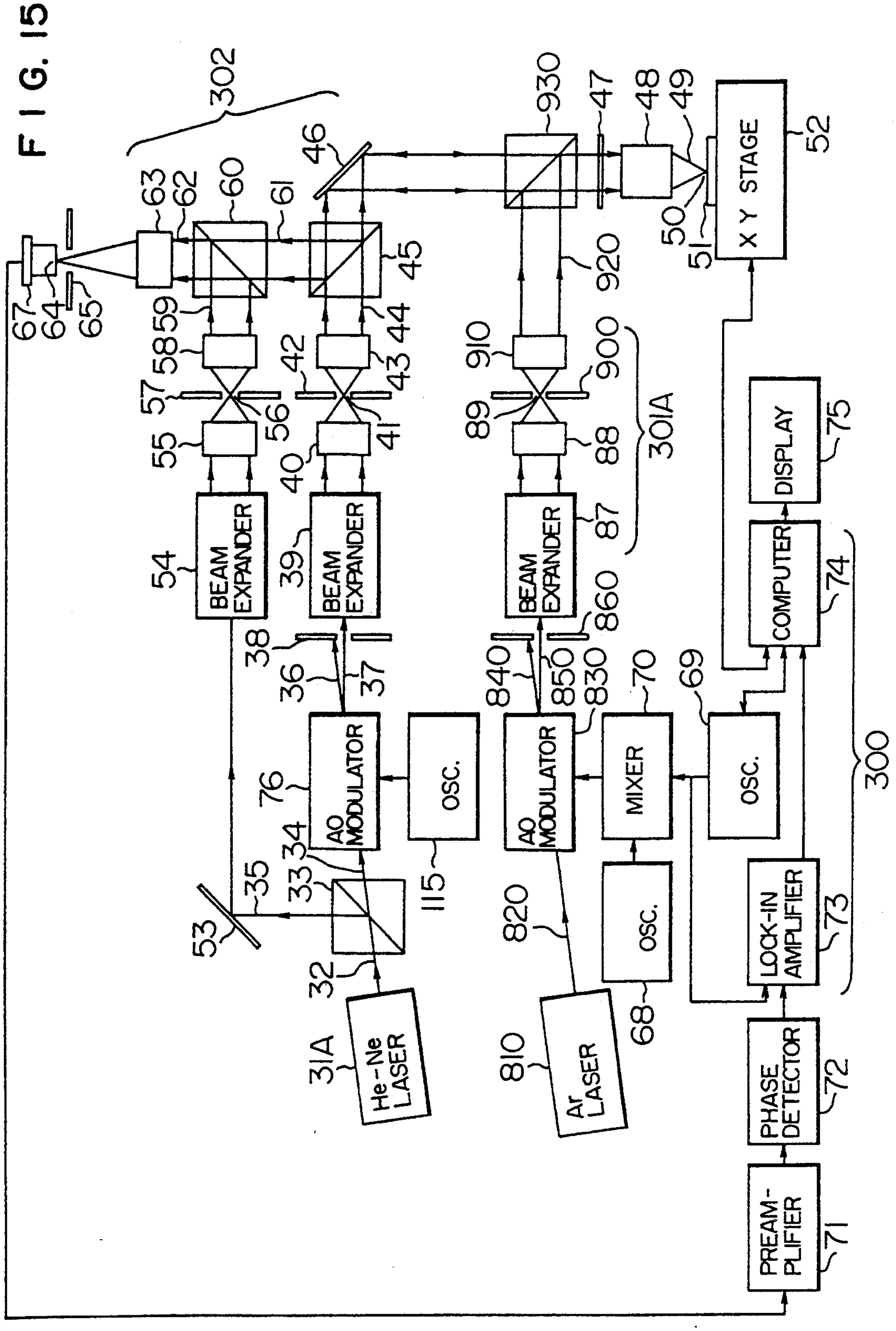
FIG. 15 is a block diagram for showing a photoacoustic detecting optical system according to a fifth embodiment of the present invention.

At first, a fifth embodiment of the present invention will be explained with reference to FIGS. 15 to 21. FIG. 15 shows a photoacoustic detecting optical system according to the fifth embodiment of the present invention. The present optical system includes an excitation optical system 301A, a heterodyne type Mach-Zehender optical interferometric system 302 for detecting a photoacoustic signal and a signal processing system 300. A parallel beam 820 is emitted from an Ar laser 810, having a wavelength of 515 nm, in the excitation optical system 301A, and the parallel beam 820 is incident to an acousto-optical modulator 830. Now referring to FIG. 15, a sinusoidal wave 100 of a frequency $f_B$ as shown in FIG. 4(*a*) and a rectangular wave 101 of a frequency $f_L$ ($f_L < f_B$) as shown in FIG. 4(*b*) are inputted to the mixer 70 from an oscillator 68 and an oscillator 69, respectively. A product of both waveforms is taken to produce a modulation signal 102 as shown in FIG. 4(*c*), and the product signal is inputted to the acousto-optical modulator 830. As a result, from the acousto-optical modulator 830, a first-order diffracted light 850 having a frequency shift of $f_B$ is intermittently outputted at the frequency $f_L$. In other words, an excitation light beam is frequency-shifted by $f_B$ and intensity-modulated by the modulation frequency $f_L$. A zero-order light 840 is shaded by a diaphragm 860. The intensity-modulated beam 850 is expanded by a beam expander 87 to have a desired beam diameter, and is then focused at a rear focal point 89 by a lens 88. A pin-hole 900 is provided at the rear focal point 89 to shade high-order diffraction light components 105*a* and 105*b* around a peak portion of the focal spot, as shown in FIG. 5(*a*), in the same manner as applied to the pin-hole 42 in FIG. 1. As a result, the light intensity distribution of the light after having passed through the pin-hole 900 exists in only the peak portion 105 as shown in FIG. 5(*b*). Since the focal point 89 is a front focal point of the lens 910, the light after having passed through the pin-hole 900 becomes a parallel light 920 after passing through the lens 910. The parallel light 920 is reflected by a dichroic prism 930, which reflects a light having a wavelength below 600 nm and passes a light having a wavelength equal to or above 600 nm. The reflected light then passes through the λ/4 plate 47 and is focused on the front focal point 50 on the sample 51 by the objective lens 48. Then, the light becomes an optical spot having the light intensity distribution which is the same as the one as shown in FIG. 5(*b*). In other words, the front focal point 89 of the lens 910 and the front focal point 50 of the objective lens 48 are mutually in a conjugate relation and are, at the same time, in a confocal relation. A thermal distortion wave generated by the photoacoustic effect on the light focused portion 50 on the sample 51 generates a thermoelastic wave, and at the same time, generates minute displacement of the light focused portion 50 on the surface of the sample 51. This minute displacement periodically changes at the intensity modulation frequency $f_L$ of the excitation light 920.

Now, in the Mach-Zehender optical interferometric system 302, the polarization direction 106 of the linear polarization beam 32 emitted from the He-Ne laser 31A (wavelength 633 nm) is set to have an angle of 45 degrees with respect to the x axis and the y axis respectively as shown in FIG. 2. Assume that the x axis is in the vertical direction relative to the paper surface of FIG. 15 and the y axis is in the direction orthogonal to the vertical direction. Then, in FIG. 15, the p-polarization component 34 (shown by 107 in FIG. 2) of the incident light beam 32 passes through the polarization beam splitter 33 and is incident to the acousto-optical modulator 76. The s-polarization component 35 (shown by 79 in FIG. 2) is reflected by the polarization beam splitter 33. A sinusoidal wave 100 of the frequency $f_B$ shown in FIG. 4(*a*) is inputted to the acousto-optical modulator 76 from the oscillator 115. As a result, the first-order diffracted light 37 after having its frequency shifted by $f_B$ is outputted from the acousto-optical modulator 76. The zero-order light 36 is shaded by the diaphragm 38. The first-order diffracted light 37 is expanded to have a desired beam diameter by the beam expander 39 and then this expanded light is focused at the rear focal point 41 by the lens 40. The pin-hole 42 is provided at the rear focal point 41 to shade high-order diffraction light components 105*a* and 105*b* around the peak portion 105 of the focused beam spot as shown in FIG. 5(*a*). As a result, the light intensity distribution immediately after having passed through the pin-hole 42 provides only the peak portion 90 as shown in FIG. 5(*b*). Since the focal point 41 is also a front focal point of the lens 43, the light from the pin-hole 42, after having passed through the lens 43, becomes a parallel light. The parallel light, consisting of the p-polarization component, passes through the polarization beam splitter 45, and is reflected by the mirror 46. Then, the light passes through a dichroic prism 930 and the λ/4 plate 47 and becomes a circularly polarized light. The light is further focused at the front focal point 50 on the sample 51 by the objective lens 48 to become a light spot having the same light intensity distribution as shown in FIG. 5(*b*). Namely, the front focal point 41 of the lens 43 and the front focal point 50 of the objective lens 48 are in a conjugate relation, and are also in a confocal relation. The reflected light from the light focused portion 50 on the sample 51 has phase information representative of minute displacement of the surface of the sample 51, and becomes a parallel light after having passed through the objective lens 48. The light further becomes an s-polarized beam after having passed through the λ/4 plate 47. The s-polarized beam again passes through the same light path and is then reflected by the polarization beam splitter 45 and passes through the non-polarization beam splitter 60.

In the mean time, the s-polarized beam 35 reflected by the polarization beam splitter 33, which is a reference light, is reflected by the mirror 53 and the reflected light is expanded to have a desired beam diameter by the beam expander 54. The light is then focused on the rear focal point 56 by the lens 55. A pin-hole 57 is provided at the rear focal point 56 to shade the high-order diffraction light components 105*a* and 105*b* around the peak portion 150 of the light focusing spot as shown in FIG. 5(*a*). As a result, the light intensity distribution immediately after having passed through the pin-hole 57 provides only the peak portion 105, as shown in FIG. 5(*b*). Since the focal point 56 is also a front focal point of the lens 58 the light from the pin-hole 57, after having passed through the lens 58, becomes a parallel reference light 59. The reference light 59, after having been reflected by the non-polarization beam splitter 60, mutually interferes with the reflected light 61 from the surface of the sample 51 which has passed through the non-polarization beam splitter 60 to produce interference light 62. This interference light 62 includes optical phase information representative of the minute displacement created on the surface of the sample 51 by the photoacoustic effect. The interference light 62 is focused on the rear focal point 64 by the lens 63 and is then detected by the photoelectric converting element 67 such as photodiode or the like. In this Mach-Zehender optical interferometric system 302, the front focal point 41 of the lens 43, the front focal point 56 of the lens 58, the front focal point 50 of the objective lens 48 and the rear focal point 64 of the lens 63 are mutually in a conjugate relation, and are at the same time in a confocal relation. Further, a pin-hole 65 is provided at the rear focal point 64 of the lens 63. As a result, it is possible to shade a stray light occurring within the objective lens 48, an interference component occurring within a transparent thin film possibly provided on the sample or a high-order diffraction light component occurring due to a fine uneven surface of the sample.

Assume the wavelength of the incident light 32 is expressed as λ, the intensity of the reflected light 61 from the surface of the sample 51 is expressed as Is, the intensity of the reference light 59 is expressed as Ir, the phase difference between the two optical paths including time variation is expressed as φ(t), the amplitude of the minute displacement of the surface of the sample 51 is expressed as a, and the phase is expressed as θ, then the intensity I' of the interference light detected by the photoelectric converting element 67 can be expressed by the following expression (7).

$$I' = Is + Ir + 2\sqrt{IsIr}\cdot \tag{7}$$

-continued $$\cos\left\{2\pi f_B t - \frac{4\pi}{\lambda}a\cdot\cos(2\pi f_L t+\theta) + \phi(t)\right\}$$

Because a<λ, the above expression (7) can be approximated by the following expression (8).

$$I' \approx Is + Ir + 2\sqrt{IsIr}\cdot\left\{\cos(2\pi f_B t + \phi(t)) + \sin(2\pi f_B t + \phi(t)) \times \frac{4\pi}{\lambda}a\cdot\cos(2\pi f_L t + \theta)\right\} \tag{8}$$

In the above expression, a·cos $(2\pi f_L t+\theta)$ is a term for expressing the minute displacement of the surface of the sample 51 generated by the photoacoustic effect. In the present embodiment, the following frequencies have been assumed: $f_B$=40 MHz, $f_L$=100 kHz.

Next explained is a method for obtaining the amplitude a and the phase θ of minute displacement of the surface of the sample 51 generated at the modulation frequency $f_L$ by the photoacoustic effect from the interference light expressed in the expression (8) by the signal processing system 300. A photoelectrically converted interference intensity signal is amplified by the preamplifier 71 and is then applied to the phase detecting circuit 72. In the phase detecting circuit 72, the interference intensity signal is separated by an in-phase power splitter 7291 into two signals as shown in FIG. 6. One of the separated signals passes through a band-pass filter 7292 having a center frequency $f_B$ and the phase of this signal is delayed by π/2 by a phase shifter 7293. An output signal from the phase shifter 7293 is amplified by an amplifier 7294 and is then applied to a mixer 7295. Then, a signal of a product of this signal and the other interference intensity signal separated by the in-phase power splitter 7291 is produced from the mixer 7295. The interference intensity signal $I'_{D1}$ from the in-phase power splitter 7291, the output signal $I'_{D2}$ from the amplifier 7294 and the output signal $I'_D$ from the mixer 7295 are expressed by the following expressions (9), (10) and (11), respectively.

$$I_{D1}' = \frac{1}{2}\left[Is + Ir + 2\sqrt{IsIr}\cdot\left\{\cos(2\pi f_B t + \phi(t)) + \sin(2\pi f_B t + \phi(t)) \times \frac{4\pi}{\lambda}a\cdot\cos(2\pi f_L t + \theta)\right\}\right] \tag{9}$$

$$I_{D2}' = \sqrt{IsIr}\cdot\{-\sin(2\pi f_B t + \phi(t)) + \cos(2\pi f_B t + \phi(t))\} \tag{10}$$

$$\begin{aligned} I_D' &= I_{D1}' \times I_{D2}' \\ &= \frac{1}{2}(Is + Ir)\cdot\sqrt{IsIr}\cdot\{-\sin(2\pi f_B t + \phi(t)) + \cos(2\pi f_B t + \phi(t))\} + \\ &\quad IsIr\left[-\frac{4\pi}{\lambda}a\cdot\cos(2\pi f_L t + \theta) + \right. \end{aligned} \tag{11}$$

-continued $$\left\{1+\frac{4\pi}{\lambda}a\cdot\cos(2\pi f_L t+\theta)\right\}\cdot \cos^2(2\pi f_B t+\phi(t))+ \left\{\frac{4\pi}{\lambda}a\cdot\cos(2\pi f_L+\theta)-1\right\}\times \cos(2\pi f_B t+\theta(t))\cdot\sin(2\pi f_B t+\phi(t))\Bigg]$$

The above expression (11) can be approximated by the following expression because $a<\lambda$.

$$I_D' \approx \frac{1}{2} IsIr - IsIr\frac{4\pi}{\lambda} a\cdot\cos(2\pi f_L t+\theta) + \frac{1}{2}(Is+Ir)\cdot\sqrt{IsIr}\cdot\{\cos(2\pi f_B t+\phi(t)) - \sin(2\pi f_B t+\phi(t))\} + \frac{1}{2} IsIr\{\cos(4\pi f_B t+2\phi(t)) - \sin(4\pi f_B t+2\phi(t))\} \quad (12)$$

The first term of the expression (12) shows the DC component, the second term shows the frequency component of $f_L$ to be detected, the third and fourth terms show the frequency component of $f_B$ and the fifth and sixth terms show the frequency component of 2 $f_B$. Now, assuming $f_L<f_B$, the output signal from the mixer 7295 is passed through the low-pass filter 7296 which blocks the frequency component equal to or above $f_B$, and then this is inputted to the lock-in amplifier 73 in FIG. 15. From the low-pass filter 7296, only the DC component and the frequency component of $f_L$ are extracted, and from the lock-in amplifier 73, the amplitude and phase of the frequency component of $f_L$ of the interference intensity signal, after having been photoelectrically converted, are finally extracted, with the rectangular wave signal of the frequency $f_L$ outputted from the oscillator 69 used as a reference signal. The amplitude a and the phase θ of the minute displacement of the surface of the sample 51 are obtained from this amplitude and this phase. The amplitude a and the phase θ have thermal and elastic information within the thermal diffusion region $V_{th}$ corresponding to the modulation frequency $f_L$. Accordingly, if there is an internal defect such as a crack within this thermal diffusion region $V_{th}$, the amplitude a and the phase θ change so that the existence of the internal defect is known. The control signal of the XY stage 52 and the output signal from the lock-in amplifier 73 are processed by the computer 74 and the photoacoustic signal at each point on the sample 51 is outputted on the monitor television display 75 as a two-dimensional photoacoustic image. By controlling the frequency $f_L$ of the modulation signal outputted from the oscillator 69 by the computer 74, various modulation frequencies can be set, thus enabling a detection of information relevant to the inside of the sample 51 at various depths.

Figure 16:
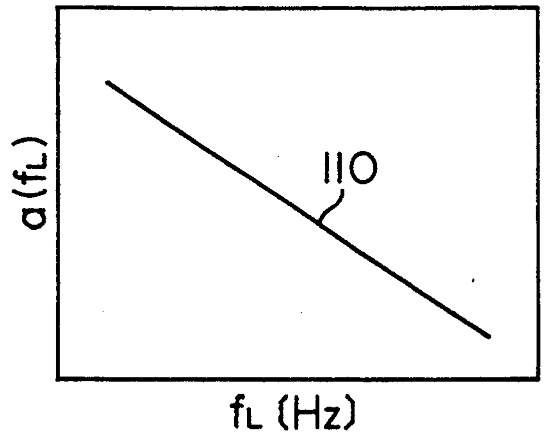
FIG. 16 is a modulation frequency characteristic diagram for showing intensity of a photoacoustic signal.
Figure 17:
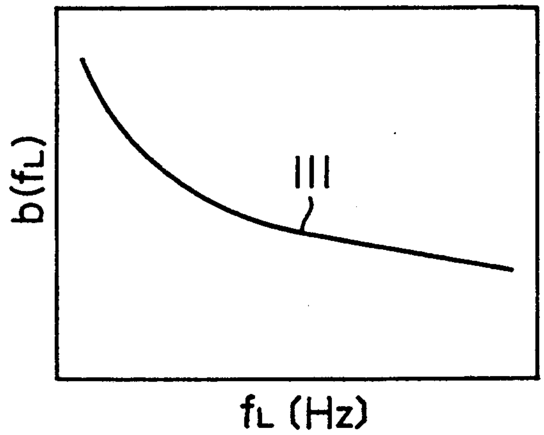
FIG. 17 is a modulation frequency characteristic diagram for showing detection sensitivity of an interference optical system.
Figure 18:
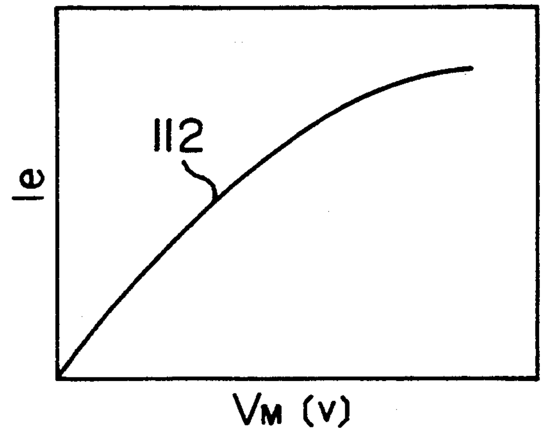
FIG. 18 is a characteristic diagram for showing a relationship between an amplitude of a modulation signal and intensity of a first order diffraction beam outputted from an acousto-optical modulator.

When the sample is optically transparent and is thermally thin, for example, the photoacoustic signal has frequency characteristic 110 wherein the signal intensity a ($f_L$) of the photoacoustic signal is inversely proportional to the intensity modulation frequency $f_L$ of the excitation light as shown in FIG. 16. Further, the detection intensity b ($f_L$) Of the Mach-Zehender optical interferometric system 302 has frequency characteristic 111 wherein the detection sensitivity b ($f_L$), which is expressed as the signal intensity of the minimum output level identified as a noise level in the detector, is inversely proportional to $\sqrt{f_L}$ where $f_L$ is a variation frequency of the surface displacement (intensity modulation frequency of the excitation light as shown in FIG. 17). Therefore, according to the conventional photoacoustic signal detector, when defects at various depths of the inside of the sample have been detected by changing the intensity modulation frequency $f_L$ of the excitation light, it is very difficult to quantify the sizes of the defects from the detected photoacoustic signal, because the detection sensitivity of the photoacoustic signal changes with the modulation frequency. Thus, according to the present embodiment, this problem is solved by the following method. First, modulation frequency characteristics for each of the photoacoustic signal and the interferometer are obtained in advance for each sample either theoretically or by experiments. In the case of the above example, the intensity of the photoacoustic signal finally obtained is proportional to the $-3/2$, i.e., $((-1)+(-\frac{1}{2}))$, power of the modulation frequency $f_L$. Therefore, in order to make the detection sensitivity constant at each modulation frequency, it is proposed to change the intensity Ie of the excitation light in proportion to the 3/2 power of the modulation frequency $f_L$ which defines a reciprocal number or characteristic of the modulation frequency characteristics. In order to change the intensity Ie of the excitation light, according to the present embodiment, the amplitude $V_M$ of the rectangular wave 101 of the frequency $f_L$ shown in FIG. 4(*b*) outputted from the oscillator 69 is changed to change the intensity Ie of the excitation light, which is the first-order diffracted light 850 outputted from the acousto-optical modulator 830, as shown by characteristic 112 in FIG. 18. Accordingly, when detecting the photoacoustic signal while changing the modulation frequency to various levels, the amplitude $V_M$ of the rectangular wave 101 of the frequency $f_L$ shown in FIG. 4(*b*) outputted from the oscillator 69 is changed in proportion to the 3/2 power of the modulation frequency $f_L$ by the control of the computer 74, and as a result the amplitude $V_M$ of the modulation signal 102 shown in FIG. 4(*c*) is changed. As a result, the intensity Ie of the excitation light 850 (105) can be changed in proportion to the 3/2 power of the modulation frequency $f_L$ for each modulation frequency as shown by characteristic 113 in FIG. 19. Thereby, the signal intensity I of the photoacoustic signal is made constant for each modulation frequency as shown by characteristic 114 in FIG. 20, thus correcting the modulation frequency characteristic of the detection sensitivity.

Figure 19:
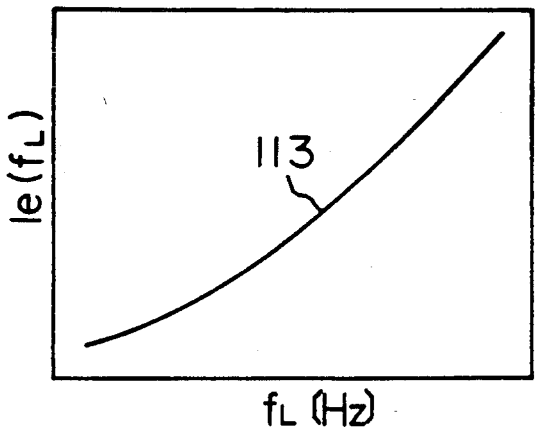
FIG. 19 is a modulation frequency characteristic diagram for showing intensity of an excitation beam for compensation of modulation frequency characteristics of a photoacoustic signal.
Figure 20:
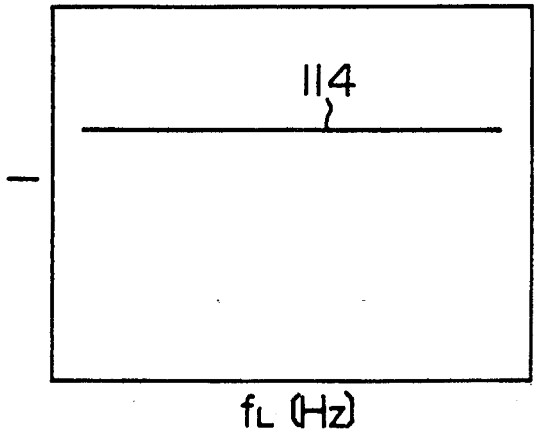
FIG. 20 is a modulation frequency characteristic diagram for showing intensity of a photoacoustic signal after compensation of the sensitivity.
Figure 22:
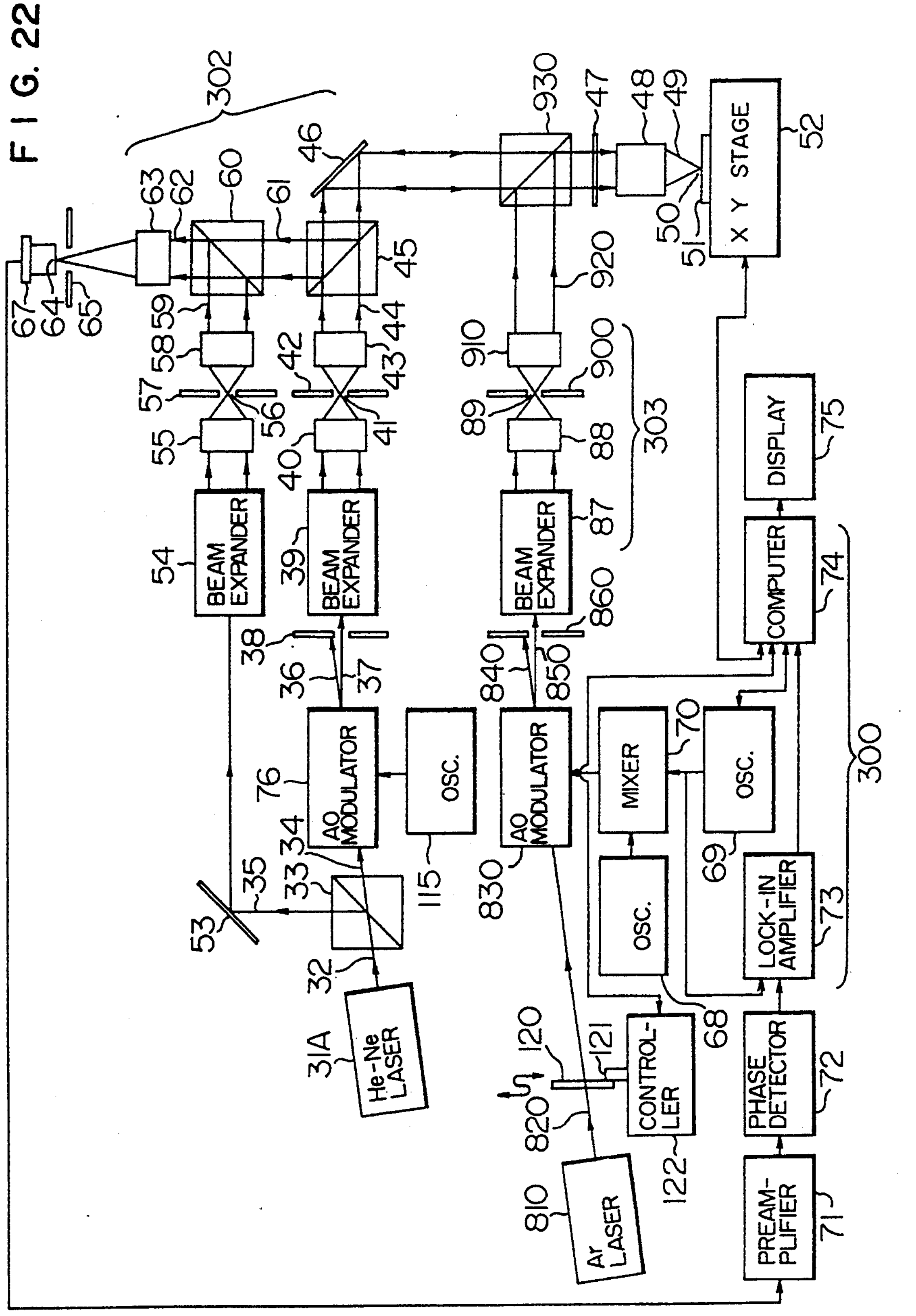
FIG. 22 is a block diagram for showing a photoacoustic detecting optical system according to a sixth embodiment of the present invention.
Figure 23A:
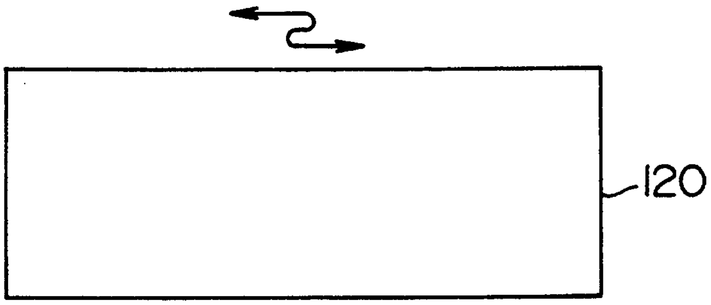
FIGS. 23(*a*)–23(*b*) are diagrams showing a continuously variable ND filter and a transmittance distribution diagram of the continuously variable ND filter in the sixth embodiment of the present invention.
Figure 23B:
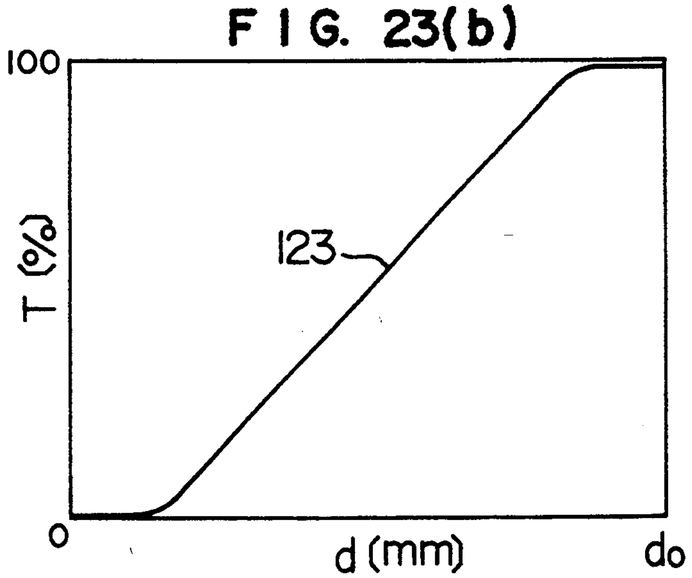

A sixth embodiment of the present invention will be explained with reference to FIGS. 22 and 23. FIG. 22 shows a photoacoustic detecting optical system according to the sixth embodiment of the present invention. The present optical system includes an excitation optical system 303, a heterodyne Mach-Zehender optical interferometric system 302 and a signal processing system 300. The basic structure and the function of the optical system are the same as those of the photoacoustic detecting optical system in the fifth embodiment shown in FIG. 15 and, therefore, their detailed explanation will be omitted. In the fifth embodiment, the amplitude $V_M$ of the modulation signal 102 shown in FIG. 4(*c*) is changed to change the intensity Ie of the first-order diffracted light 850 outputted from the acousto-optical modulator 830, i.e. the excitation light having the modulation frequency $f_L$, to thereby adjust the modulation frequency characteristic of the detected photoacoustic signal intensity I. However, in the sixth embodiment, a continuously variable $N_D$ filter 120 is shown in FIG. 23(*a*), in which the transmittance varies continuously in one direction as shown by 123 in FIG. 23(*b*), is inserted in front of the acousto-optical modulator 830 of the excitation optical system as shown in FIG. 22, and this $N_D$ filter 120 is minutely moved in the direction of the arrows by a drive mechanism 121 made of a pulse motor and a crank mechanism (not shown) and a controller 122, to thereby change the intensity Ie of the excitation light. In other words, when detecting a photoacoustic signal while changing the modulation frequency $f_L$, the continuously variable $N_D$ filter 120 is minutely moved for each modulation frequency, to change the intensity Ie of the excitation light in proportion to the 3/2 power of the modulation frequency $f_L$ as shown by characteristic 113 in FIG. 19 and adjust or compensate the modulation frequency characteristic of the photoacoustic signal. With this arrangement, the photoacoustic signal (signal intensity I) or the modulation frequency characteristic of the detection sensitivity can be made constant as shown in FIG. 20 in the same manner as in the fifth embodiment.

Further, according to the present embodiment, the continuously variable $N_D$ filter 120 separately provided in the optical path of the excitation optical system 303 is used as a unit for changing the intensity Ie of the excitation light, so that the control of the amplitude $V_M$ of the rectangular wave 101 of the frequency $f_L$ shown in 4(*b*) is not necessary in the oscillator 69, thus facilitating the circuit structure.

Figure 24:
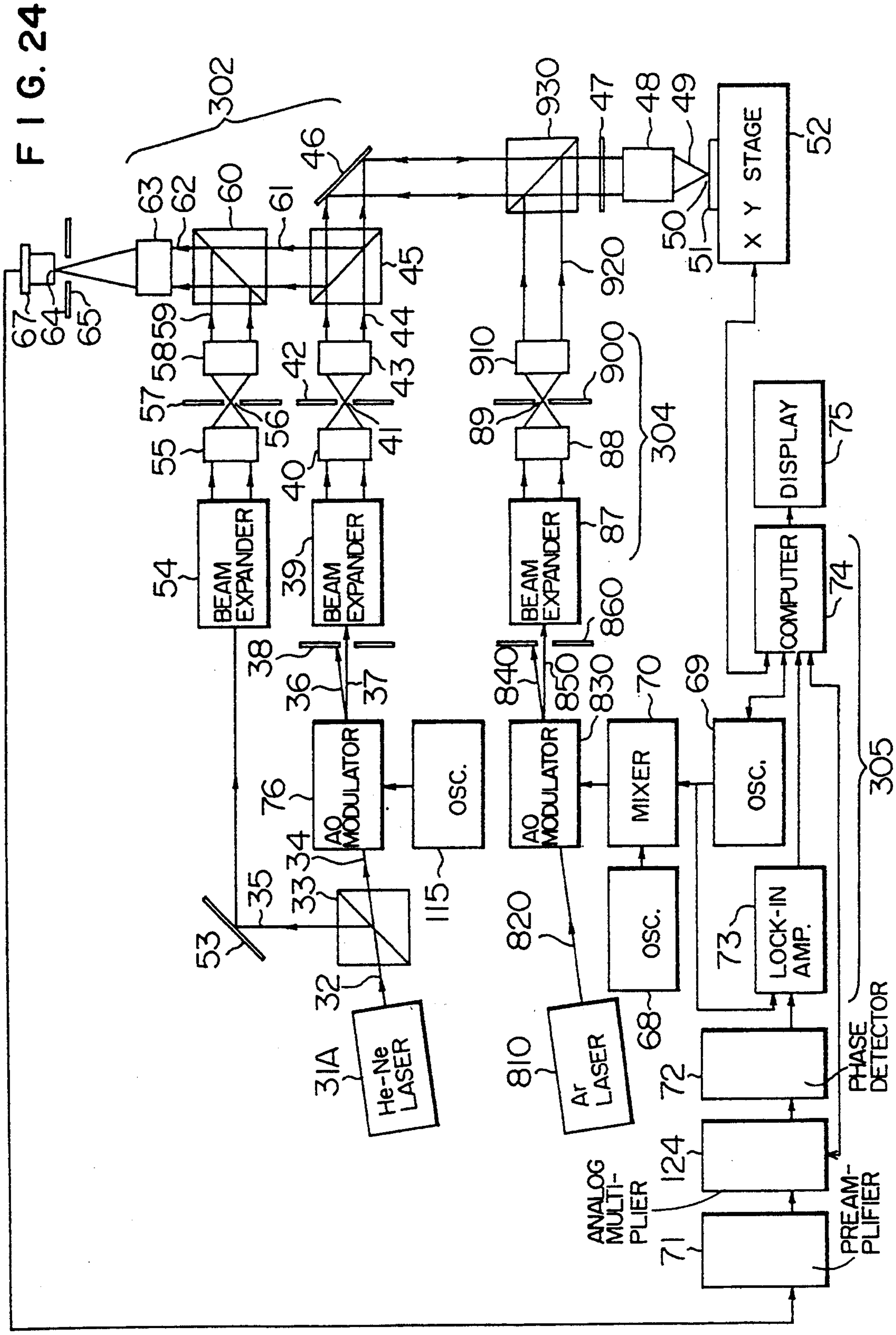
FIG. 24 is a block diagram for showing a photoacoustic detecting optical system according to a seventh embodiment of the present invention.

A seventh embodiment of the present invention will be explained below with reference to FIG. 24. FIG. 24 shows a photoacoustic detecting optical system according to the seventh embodiment of the present invention. The present optical system comprises an excitation optical system 304, a heterodyne Mach-Zehender optical interferometric system 302 and a signal processing system 305. The basic structure and the function of this optical system are the same as those of the photoacoustic detecting optical system in the fifth embodiment shown in FIG. 15, so that their detailed explanation will be emitted. In the fifth embodiment, the amplitude $V_M$ of the modulation signal 102 shown in FIG. 4(*c*) is changed to change the intensity Ie of the first-order diffracted light 850 outputted from the acousto-optical modulator 830, i.e. the excitation light, to thereby adjust or compensate the modulation frequency characteristic of the detected photoacoustic signal intensity I. However, according to the seventh embodiment, the modulation frequency characteristics of the photoacoustic signal intensity I is adjusted or compensated not by adjusting the intensity Ie of the excitation light but by an analog multiplier 124 newly provided in the signal processing system 305. In other words, when detecting a photoacoustic signal while changing the modulation frequency $f_L$ to various levels, an adjustment voltage signal corresponding to characteristic 113 in FIG. 19 is inputted to the analog multiplier 124 from the computer 74 for each modulation frequency, and the detected interference intensity signal is multiplied by this adjustment voltage signal. With this arrangement, the photoacoustic signal (signal intensity I), i.e. the modulation frequency characteristic of the detection sensitivity, can be made constant as shown by characteristic 114 in FIG. 20 in the same manner as in the fifth embodiment.

In the present embodiment, the modulation frequency characteristic of the photoacoustic signal intensity I' is electrically adjusted and compensated by using the analog multiplier 124 provided in the signal processing system 305. Therefore, it is not necessary to provide a control function for controlling the intensity of the excitation light in the excitation optical system 304, thus increasing the stability of the optical system.

Figure 26:
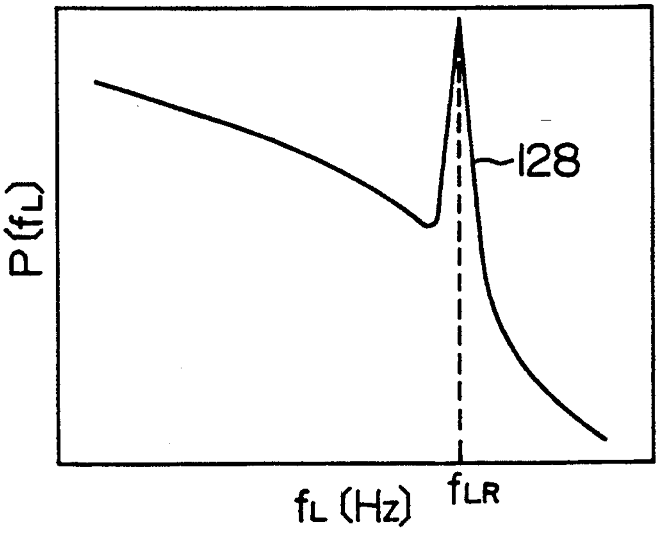
FIG. 26 is a modulation frequency characteristic diagram for showing detection sensitivity of a PZT element in the eighth embodiment of the present invention.
Figure 25:
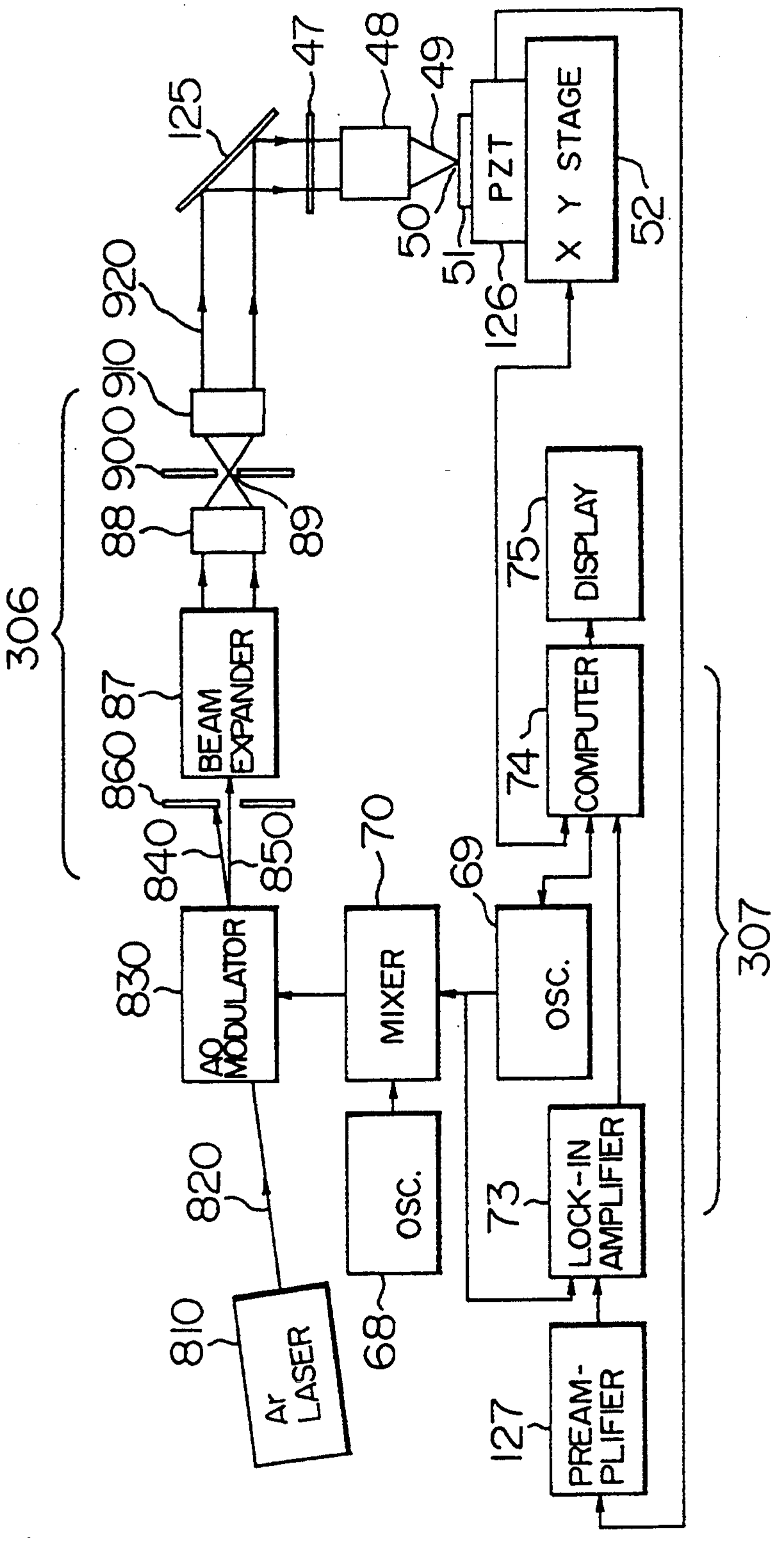
FIG. 25 is a block diagram for showing a photoacoustic detecting optical system according to an eighth embodiment of the present invention.
Figure 27:
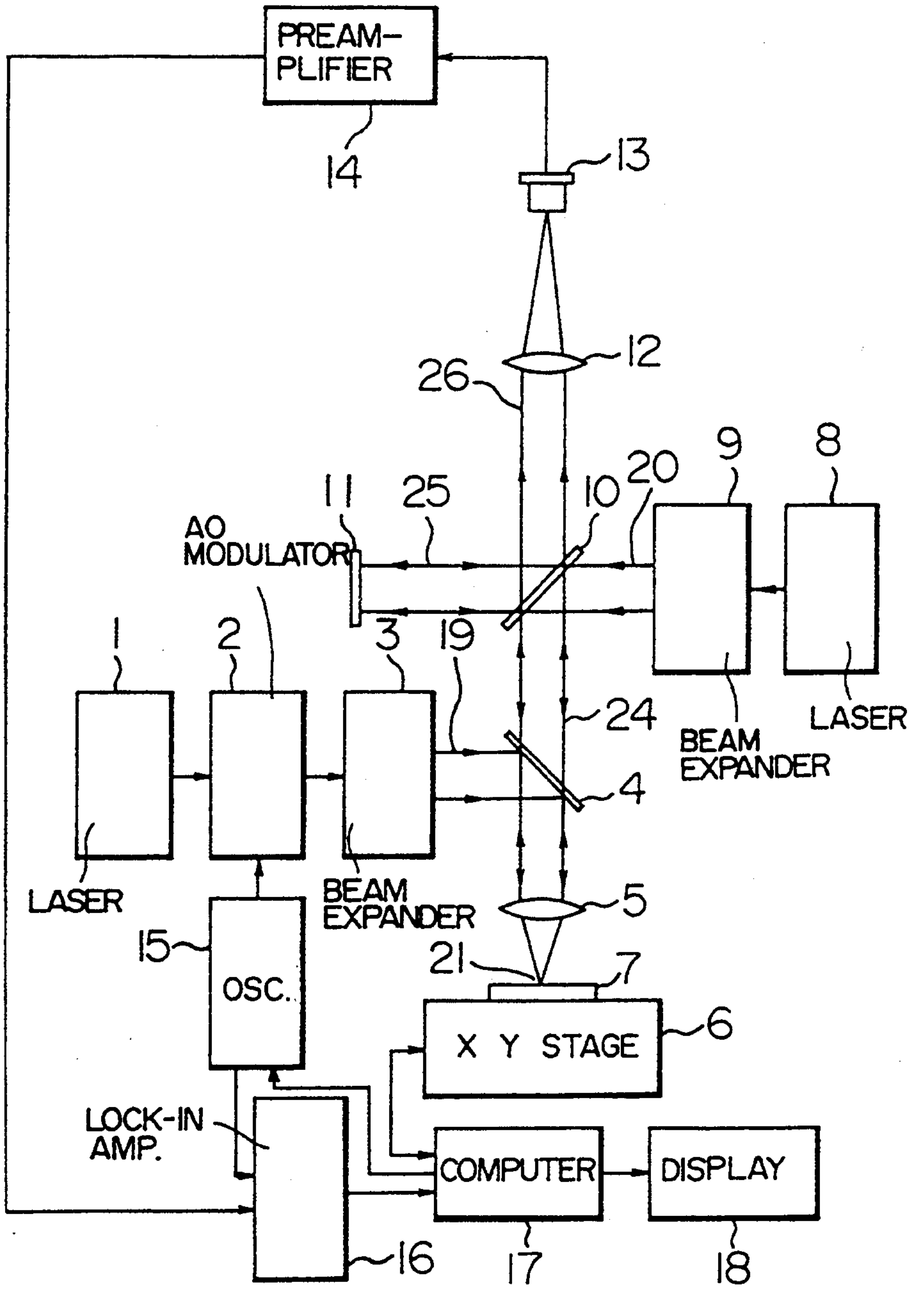
FIG. 27 is a block diagram for explaining a conventional photoacoustic detecting optical system.

An eighth embodiment of the present invention will be explained below with reference to FIGS. 25 and 26. FIG. 25 shows a photoacoustic detecting optical system according to the eighth embodiment of the present invention. The present optical system comprises an excitation optical system 306 and a signal processing system 307 including a PZT element 126 for detecting a photoacoustic signal. The structure of the excitation optical system 306 is the same as that of the excitation optical system 301A according to the fifth embodiment shown in FIG. 15, so that their detailed explanation will be omitted. Instead of the dichroic prism 93, a mirror 125 is used. While the heterodyne Mach-Zehender optical interferometric system is used for the detection of a photoacoustic signal in the fifth to the seventh embodiments, the PZT element 126 mounted on the rear surface of the sample 51 is used in the present embodiment. An output voltage from the PZT element 126, after having been amplified by a preamplifier 127, is sent to the lock-in amplifier 73. In the lock-in amplifier 73, the amplitude and the phase of the frequency component of $f_L$ are extracted from the output signal of the PZT element, with the rectangular wave signal of the frequency $f_L$ outputted from the oscillator 69 as a reference signal. The amplitude a and the phase $\theta$ of the minute displacement on the surface of the sample 51 are obtained from this amplitude and this phase. The amplitude a and the phase $\theta$ have thermal and elastic information within the thermal diffusion region $V_{th}$ defined by the modulation frequency $f_L$. Accordingly, if an internal defect such as a crack or the like exists within the thermal diffusion region $V_{th}$, the amplitude a and the phase $\theta$ change, so that the existence of the defect is known. In the same manner as the fifth embodiment, the control signal of the XY stage 52 and the output signal from the lock-in amplifier 73 are processed by the computer 74, and the photoacoustic signal at each point on the sample 51 is outputted as a two-dimensional photoacoustic image on the monitor television display 75. Further, the frequency $f_L$ of the modulation signal outputted from the oscillator 69 can be controlled by the computer 74 to be set to various modulation frequencies, thus enabling a detection of information relevant to the inside of the sample 51 at various depths.

In the present embodiment, the PZT element 126 is used to detect a photoacoustic signal. With this arrangement, both the modulation frequency characteristic 110 of the photoacoustic signal intensity a ($f_L$) shown in FIG. 16 and the modulation frequency characteristic 128 of the sensitivity p ($f_L$) of the PZT element 126 shown in FIG. 26 are adjusted in the following manner. At first, the modulation frequency characteristic 110 of the photoacoustic signal intensity a ($f_L$) shown in FIG. 16 and the modulation frequency characteristic 128 of the sensitivity p ($f_L$) of the PZT element 126 shown in FIG. 26 are measured in advance either theoretically or by experiments. Then, a reciprocal number (a compensation coefficient) of each of the measured frequency characteristics is obtained by the computer 74 so that the detection sensitivity at each modulation frequency becomes constant as shown by characteristic 114 in FIG. 20. Next, the amplitude $V_M$ of the modulation signal 101 shown in FIG. 4(*b*) outputted from the oscillator 69 is controlled by the computer 74 based on the compensation coefficient, and the amplitude $V_M$ of the modulation signal 102 shown in FIG. 4(*c*) is changed. Thus, the intensity Ie of the first-order diffracted light 850 outputted from the acousto-optical modulator 830, i.e. the excitation light, is changed, to thereby compensate the modulation frequency characteristic of the photoacoustic signal intensity I detected.

As described above, according to the fifth, sixth, seventh and eighth embodiments of the present invention, the detection sensitivity of the photoacoustic signal can be made always constant regardless of the modulation frequency of the excitation light. Therefore, when defects of a sample at various depths inside the sample have been detected by changing the modulation frequency, sizes of the defects can be discriminated from the detected photoacoustic signal. At the same time, information relative to the surface and subsurface of the sample can also be detected stably and the information relative to the subsurface of the sample at various depths detected by changing the modulation frequency can also be analyzed quantitatively.

Figure 21:
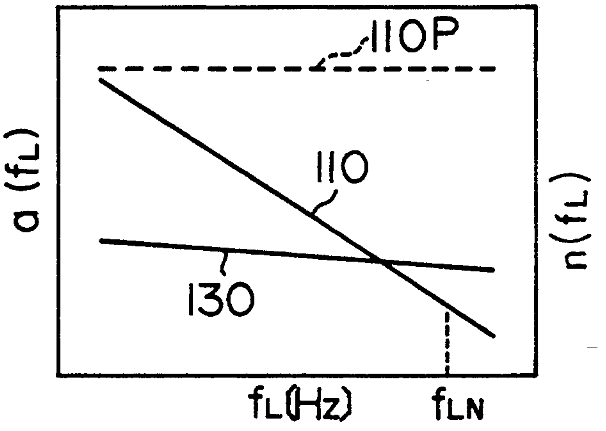
FIG. 21 is a diagram for showing modulation frequency characteristics of the intensity of a photoacoustic signal before and after compensation of the sensitivity and modulation frequency characteristics of non-optical noise.

Further, according to the fifth, sixth and eighth embodiments of the present invention, the following large advantages can be obtained. Referring to FIG. 21, when the frequency characteristic of non-optical noise, such as oscillation noises at a stage, for example, are expressed by a line 130 while the frequency characteristic of the signal intensity $a(f_L)$ of the photoacoustic signal is expressed by a line 110, the photoacoustic signal $a(f_{LN})$ becomes smaller than the noise level $n(f_{LN})$ at the modulation frequency $f_{LN}$, making it impossible to detect the photoacoustic signal $a(f_{LN})$. In such a case, these embodiments are made to change the intensity Ie of the excitation light in order to increase the intensity of the photoacoustic signal to be higher than the noise level, in particular near $f_{LN}$, and to adjust the photoacoustic signal intensity to be constant as shown by 110P in FIG. 21 regardless of variations in the modulation frequency $f_L$. Thus, the photoacoustic signal intensity $a(f_{LN})$ can be increased and detected at the modulation frequency $f_{LN}$ without increasing such non-optical noise $n(f_{LN})$.

Further, according to the fifth and eighth embodiments, a method is employed to change the amplitude $V_M$ of the modulation signal 102 of the acousto-optical modulator 830 used for modulating the intensity of the excitation light. Therefore, there is the advantage that the conventional optical system can be used as it is.

Further, according to the eighth embodiment, the PZT element is used to detect the photoacoustic signal, so that the optical system can be simplified and the adjustment of the optical axis is facilitated, or the stability of the optical system can be increased.

Further, according to the fifth to the eighth embodiments, the excitation optical system is structured as a confocal optical system. Therefore, it is possible to form on the sample a spot light having an ideal peak portion without any unnecessary high-order diffraction light components. As a result, resolution of the photoacoustic signal in the lateral direction, detection sensitivity and signal to noise ratio can be improved. Further, according to the fifth to the seventh embodiments, it is possible to shade a stray light occurring within the objective lens 48, an interference component occurring within the transparent thin film on the sample, for example within the transparent thin film forming a protection film on the semiconductor wafer sample, or a high-order diffraction light component occurring due to a minute unevenness on the surface of the sample.

As explained above, according to one aspect of the present invention, in the photoacoustic signal detecting apparatus, one of two light beams having mutually different optical frequencies is intensity modulated and focused on the sample to generate a photoacoustic effect, and reflected light from the sample and the other light beam are made to interfere with each other and a double modulation frequency component is detected. As a result, it is possible to generate a photoacoustic effect and to detect minute displacement on the surface of the sample generated by the photoacoustic effect by using one light beam. Thus, the photoacoustic signal can be accurately detected at the excited part on the sample. Further, relative adjustment of optical axis between the excitation light and the probe light is not necessary, and the information relative to the surface and subsurface or inside of the sample can be detected with high sensitivity in a simple structure of the optical system.

Further, an exciting unit for focusing the excitation light on the sample and an optical interference detecting unit for detecting minute displacement on the surface of the sample generated by the photoacoustic effect are structured as a confocal optical system. Therefore, it is possible to form a spot light having an ideal peak portion without unnecessary high-order diffraction light components on the sample and on the interference light detecting unit. Further, resolution of the photoacoustic signal in the lateral direction, the detection sensitivity and the signal to noise ratio can be improved.

According to another aspect of the present invention, in the photoacoustic signal detecting apparatus, the detection sensitivity of the photoacoustic signal becomes always constant regardless of the modulation frequency of the excitation light. Therefore, when defects of a sample at various depths inside the sample have been detected by changing the modulation frequency, it is possible to quantitatively decide sizes of the defects from the detected photoacoustic signal. At the same time, information relative to the surface and inside of the sample can be detected stably, and the information inside the sample at various depths of the sample which have been detected by changing the modulation frequency can also be analyzed quantitatively.

Further, an excitation optical unit for focusing the excitation light on the sample and an optical interference detecting unit for detecting minute displacement (thermal distortion) on the surface of the sample generated by the photoacoustic effect or the photothermal effect are structured as a confocal optical system. Therefore, it is possible to form a spot light having an ideal peak portion without unnecessary high-order diffraction light components on the sample or on the interference light detecting unit. Further, resolution of the photoacoustic signal in the lateral direction, detection sensitivity and signal to noise ratio can be improved.

I claim:

1. A photoacoustic signal detection method for detecting information about a characteristic of a surface of a sample and a subsurface of the sample, comprising the steps of:

splitting a light beam from a single light source into an excitation/probe light beam and a reference light beam;

intensity-modulating the excitation/probe light beam at a desired intensity modulation frequency to produce an intensity-modulated excitation/probe light beam for exciting and probing the surface of the sample and the subsurface of the sample;

producing an optical frequency difference between the intensity-modulated excitation/probe light beam and the reference light beam;

focusing the intensity-modulated excitation/probe light beam on the surface of the sample to generate a photoacoustic effect or a photothermal effect at the surface of the sample, thereby producing thermal distortions in the sample, wherein the intensity-modulated excitation/probe light beam is reflected from the surface of the sample to produce a reflected intensity-modulated excitation/probe light beam representative of the thermal distortions in the sample;

causing heterodyne interference to occur between the reflected intensity-modulated excitation/probe light beam and the reference light beam to produce heterodyne interference light including a frequency component having a frequency equal to twice the intensity modulation frequency, the heterodyne interference occurring as a result of the optical frequency difference between the excitation/probe light beam and the reference light beam;

converting the heterodyne interference light to an electric signal including a frequency component having a frequency equal to twice the intensity modulation frequency;

extracting from the electric signal at least one of an amplitude and a phase of the frequency component having the frequency equal to twice the intensity modulation frequency; and detecting information about the characteristic of the surface of the sample and the subsurface of the sample based on the extracted at least one of the amplitude and the phase.

2. A method according to claim 1, wherein the single light source includes a laser source for emitting a linearly-polarized light beam.

3. A method according to claim 1, wherein the step of producing an optical frequency difference between the intensity-modulated excitation/probe light beam and the reference light beam includes shifting an optical frequency of the intensity-modulated excitation/probe light beam with an acousto-optical modulator to produce the optical frequency difference.

4. A method according to claim 1, wherein the step of extracting from the electric signal at least one of an amplitude and a phase is performed with a lock-in amplifier operating based on the electric signal and a signal having a frequency equal to twice the intensity modulation frequency.

5. A method according to claim 1, wherein the optical frequency difference between the intensity-modulated excitation/probe light beam and the reference light beam is higher than the intensity modulation frequency.

6. A method according to claim 1, wherein the step of producing an optical frequency difference between the intensity-modulated excitation/probe light beam and the reference light beam includes shifting an optical frequency of only one of the intensity-modulated excitation/probe light beam and the reference light beam to produce the optical frequency difference.

7. A method according to claim 1, wherein the step of producing an optical frequency difference between the intensity-modulated excitation/probe light beam and the reference light beam includes shifting respective optical frequencies of the intensity-modulated excitation/probe light beam and the reference light beam by mutually different amounts to produce the optical frequency difference.

8. A method according to claim 1, wherein the step of focusing the intensity-modulated excitation/probe light beam on the surface of the sample is performed with focusing means;

wherein the step of causing heterodyne interference to occur is performed with means for causing heterodyne interference to occur; and wherein the focusing means and the means for causing heterodyne interference to occur are formed as a confocal optical system.

9. A photoacoustic signal detection apparatus for detecting information about a characteristic of a surface of a sample and a subsurface of the sample, comprising:

a single light source for emitting a light beam;

means for splitting the light beam into an excitation/-probe light beam and a reference light beam;

intensity modulating means for intensity-modulating the excitation/probe light beam at a desired intensity modulation frequency to produce an intensity modulated excitation/probe light beam for exciting and probing a surface of a sample and a subsurface of the sample;

means for producing an optical frequency difference between the intensity-modulated excitation/probe light beam and the reference light beam;

means for focusing the intensity-modulated excitation/probe light beam on the surface of the sample to generate a photoacoustic effect or a photothermal effect at the surface of the sample, thereby producing thermal distortions in the sample, wherein the excitation/probe light beam is reflected from the surface of the sample to produce a reflected intensity-modulated excitation/probe light beam representative of the thermal distortions in the sample;

means for causing heterodyne interference to occur between the reflected intensity-modulated excitation/probe light beam and the reference light beam to produce heterodyne interference light including a frequency component having a frequency equal to twice the intensity modulation frequency, the heterodyne interference occurring as a result of the optical frequency difference between the excitation/probe light beam and the reference light beam;

means for converting the heterodyne interference light to an electric signal including a frequency component having a frequency equal to twice the intensity modulation frequency;

means for extracting from the electric signal at least one of an amplitude and a phase of the frequency component having the frequency equal to twice the intensity modulation frequency; and means for detecting information about the characteristic of the surface of the sample and the subsurface of the sample based on the extracted at least one of the amplitude and the phase.

10. An apparatus according to claim 9, wherein the single light source includes a laser source for emitting a linearly-polarized light beam.

11. An apparatus according to claim 9, wherein the means for producing an optical frequency difference between the intensity-modulated excitation/probe light beam and the reference light beam includes means for shifting an optical frequency of the intensity-modulated excitation/probe light beam with the intensity modulating means to produce the optical frequency difference.

12. An apparatus according to claim 9, wherein the means for extracting from the electric signal at least one of an amplitude and a phase includes a lock-in amplifier operating based on the electric signal and a signal having a frequency equal to twice the intensity modulation frequency.

13. An apparatus according to claim 9, wherein the optical frequency difference between the intensity-modulated excitation/probe light beam and the reference light beam is higher than the intensity modulation frequency.

14. An apparatus according to claim 9, wherein the means for producing an optical frequency difference between the intensity-modulated excitation/probe light beam and the reference light beam includes means for shifting an optical frequency of only one of the intensity-modulated excitation/probe light beam and the reference light beam to produce the optical frequency difference.

15. An apparatus according to claim 9, wherein the means for producing an optical frequency difference between the intensity-modulated excitation/probe light beam and the reference light beam includes means for shifting respective optical frequencies of the intensity-modulated excitation/probe light beam and the reference light beam by mutually different amounts to produce the optical frequency difference.

16. An apparatus according to claim 9, wherein the means for focusing and the means for causing heterodyne interference to occur are formed as a confocal optical system.

17. A photoacoustic signal detection method for detecting information about a characteristic of a surface of a sample and various depths in a subsurface of the sample, comprising the steps of:

intensity-modulating a light beam at a desired intensity modulation frequency to produce an intensity-modulated light beam, the intensity modulation frequency being selected in accordance with a thermal diffusion length in the sample corresponding to a depth in the subsurface of the sample about a characteristic of which information is to be detected;

focusing the intensity-modulated light beam on the surface of the sample to generate a photoacoustic effect or a photothermal effect at the surface of the sample, thereby producing thermal distortions in the sample;

detecting the thermal distortions in the sample and producing a thermal distortion signal representative of the thermal distortions in the sample, the thermal distortion signal including a component having a frequency related to the intensity modulation frequency, wherein variations in the intensity modulation frequency produce variations in an amplitude of the component having a frequency related to the intensity modulation frequency;

compensating for the variations in the amplitude of the component having a frequency related to the intensity modulation frequency such that the amplitude of the component having a frequency related to the intensity modulation frequency is unaffected by the variations in the intensity modulation frequency; and extracting from the thermal distortion signal the amplitude of the component having a frequency related to the intensity modulation frequency which is unaffected by the variations in the intensity modulation frequency.

18. A method according to claim 17, wherein the amplitude of the component having a frequency related to the intensity modulation frequency has a sensitivity characteristic which is a function of the intensity modulation frequency; and wherein the step of compensating for the variations in the amplitude of the component having a frequency related to the intensity modulation frequency includes adjusting an intensity of the intensity-modulated light in accordance with the intensity modulation frequency such that the sensitivity characteristic of the amplitude of the component having a frequency related to the intensity modulation frequency is substantially constant at each intensity modulation frequency.

19. A method according to claim 17, wherein the amplitude of the component having a frequency related to the intensity modulation frequency has a sensitivity characteristic which is a function of the intensity modulation frequency; and wherein the step of compensating for the variations in the amplitude of the component having a frequency related to the intensity modulation frequency includes adjusting a level of the thermal distortion signal in accordance with the intensity modulation frequency such that the sensitivity characteristic of the amplitude of the component having a frequency related to the intensity modulation frequency is substantially constant at each intensity modulation frequency.

20. A method according to claim 17, wherein the step of detecting the thermal distortions in the sample and producing a thermal distortion signal representative of the thermal distortions in the sample includes detecting the thermal distortions in the sample with thermal distortion detecting means having a detection sensitivity characteristic which is a function of the intensity modulation frequency;

wherein the thermal distortion signal has a sensitivity characteristic which is a function of the intensity modulation frequency; and wherein the step of compensating for the variations in the amplitude of the component having a frequency related to the intensity modulation frequency includes compensating for the detection sensitivity characteristic of the thermal distortion detecting means such that the sensitivity characteristic of the thermal distortion signal is substantially constant at each intensity modulation frequency.

21. A method according to claim 17, wherein the step of detecting the thermal distortions in the sample and producing a thermal distortion signal representative of the thermal distortions in the sample includes detecting the thermal distortions in the sample on the surface of the sample with optical interference detecting means.

22. A method according to claim 21, wherein the optical interference detecting means is formed as a confocal optical system for detecting the thermal distortions in the sample on the surface of the sample.

23. A method according to claim 17, wherein the step of detecting the thermal distortions in the sample and producing a thermal distortion signal representative of the thermal distortions in the sample includes detecting the thermal distortions in the sample on the surface of the sample with a piezoelectric transducer.

24. A method according to claim 17, wherein the step of focusing the intensity-modulated light beam on the surface of the sample to generate a photoacoustic effect or a photothermal effect at the surface of the sample includes focusing the intensity-modulated light beam on the surface of the sample with focusing means which is formed as a confocal optical system.

25. A photoacoustic signal detection apparatus for detecting information about a characteristic of a surface of a sample and various depths in a subsurface of the sample, comprising:

means for intensity-modulating a light beam at a desired intensity modulation frequency to produce an intensity-modulated light beam, the intensity modulation frequency being selected in accordance with a thermal diffusion length in a sample corresponding to a depth in a subsurface of the sample about a characteristic of which information is to be detected;

means for focusing the intensity-modulated light beam on the surface of the sample to generate a photoacoustic effect or a photothermal effect at the surface of the sample, thereby producing thermal distortions in the sample;

means for detecting the thermal distortions in the sample and producing a thermal distortion signal representative of the thermal distortions in the sample, the thermal distortion signal including a component having a frequency related to the intensity modulation frequency, wherein variations in the intensity modulation frequency produce variations in an amplitude of the component having a frequency related to the intensity modulation frequency;

means for compensating for the variations in the amplitude of the component having a frequency related to the intensity modulation frequency such that the amplitude of the component having a frequency related to the intensity modulation frequency is unaffected by the variations in the intensity modulation frequency; and means for extracting from the thermal distortion signal the amplitude of the component having a frequency related to the intensity modulation frequency which is unaffected by the variations in the intensity modulation frequency.

26. An apparatus according to claim 25, wherein the amplitude of the component having a frequency related to the intensity modulation frequency has a sensitivity characteristic which is a function of the intensity modulation frequency; and wherein the means for compensating for the variations in the amplitude of the component having a frequency related to the intensity modulation frequency includes means for adjusting an intensity of the intensity-modulated light in accordance with the intensity modulation frequency such that the sensitivity characteristic of the amplitude of the component having a frequency related to the intensity modulation frequency is substantially constant at each intensity modulation frequency.

27. An apparatus according to claim 25, wherein the amplitude of the component having a frequency related to the intensity modulation frequency has a sensitivity characteristic which is a function of the intensity modulation frequency; and wherein the means for compensating for the variations in the amplitude of the component having a frequency related to the intensity modulation frequency includes means for adjusting a level of the thermal distortion signal in accordance with the intensity modulation frequency such that the sensitivity characteristic of the amplitude of the component having a frequency related to the intensity modulation frequency is substantially constant at each intensity modulation frequency.

28. An apparatus according to claim 25, wherein the means for detecting the thermal distortions in the sample and producing a thermal distortion signal representative of the thermal distortions in the sample includes thermal detecting distortion means for detecting the thermal distortions in the sample, the thermal distortion detecting means having a detection sensitivity characteristic which is a function of the intensity modulation frequency;

wherein the thermal distortion signal has a sensitivity characteristic which is a function of the intensity modulation frequency; and wherein the means for compensating for the variations in the amplitude of the component having a frequency related to the intensity modulation frequency includes means for compensating for the detection sensitivity characteristic of the thermal distortion detecting means such that the sensitivity characteristic of the thermal distortion signal is substantially constant at each intensity modulation frequency.

29. An apparatus according to claim 25, wherein the means for detecting the thermal distortions in the sample and producing a thermal distortion signal representative of the thermal distortions in the sample includes optical interference detecting means for detecting the thermal distortions in the sample on the surface of the sample.

30. An apparatus according to claim 29, wherein the optical interference detecting means is formed as a confocal optical system for detecting the thermal distortions in the sample on the surface of the sample.

31. An apparatus according to claim 25, wherein the means for detecting the thermal distortions in the sample and producing a thermal distortion signal representative of the thermal distortions in the sample includes a piezoelectric transducer for detecting the thermal distortions in the sample on the surface of the sample.

32. An apparatus according to claim 25, wherein the means for focusing the intensity-modulated light beam on the surface of the sample to generate a photoacoustic effect or a photothermal effect at the surface of the sample is formed as a confocal optical system.

* * * * *